United States Patent [19]

Papsidero

[11] Patent Number: 5,185,147
[45] Date of Patent: Feb. 9, 1993

[54] SHORT POLYPEPTIDE SEQUENCES USEFUL IN THE PRODUCTION AND DETECTION OF ANTIBODIES AGAINST HUMAN IMMUNODEFICIENCY VIRUS

[75] Inventor: Lawrence D. Papsidero, Orchard Park, N.Y.

[73] Assignee: Cellular Products, Inc., Buffalo, N.Y.

[21] Appl. No.: 234,381

[22] Filed: Aug. 19, 1988

[51] Int. Cl.$^5$ ................ A61K 39/12; A61K 39/21; C07K 7/00

[52] U.S. Cl. .................. 424/89; 424/88; 424/85.8; 530/326; 530/327; 530/328; 530/329; 530/402; 530/403; 530/387.9; 530/826; 530/388.35; 530/387.2; 514/13; 514/14; 514/15; 514/16; 514/17; 435/240.27

[58] Field of Search .......... 424/85.8, 89, 88, 85.8; 530/387, 326–329, 402, 403, 387, 826; 514/13, 14, 15, 16, 17; 435/240.27

[56] References Cited

U.S. PATENT DOCUMENTS 4,843,011 6/1989 Sarngadharan ............ 530/388.35
4,983,387 1/1991 Goldstein ...................... 424/88

FOREIGN PATENT DOCUMENTS 0273716 7/1988 European Pat. Off.
8602383 10/1985 PCT Int'l Appl.

OTHER PUBLICATIONS

H. M. Geysen et al., "Strategies for epitope analysis using peptide synthesis", J. Immunol. Meth., 102, 259–274 (1987).
G. Walter, "Production and use of antibodies against synthetic peptides", J. Immunol. Meth., 88, 149–161 (1986).
R. Jemmerson et al., "Mapping Antigenic Sites on Proteins: Implications for the Design of Synthetic Vaccines", BioTechniques, vol. 4, 18–31 (1986).
T. P. Hopp et al., "Prediction of Protein antigenic determinants from amino acid sequences", Proc. Natl. Acad. Sci., USA, 78, 3824–3828 (1981).
C. L. Parravicini et al., "Monoclonal Antibodies to the Human Immunodeficiency Virus p18 cross-react with normal Human Tissues", AIDS, 2, 171–177 (1988).
P. S. Sarin et al., "Neutralization of HTLV-III/LAV Replication by Antiserum to Thymosinα", Science, 232, 1135–1137 (1986).
P. H. Naylor et al., "Human immunodeficiency virus contains an epitope immunoreactive with thymosinα, and the 30-amino acid synthetic p17 group-specific antigen peptide HGP-30" Proc. Natl. Acad. Sci., USA, 84, pp. 2951–2955 (1987).
J. Ritter et al., "Lack of reactivity of anti-human immunodeficiency virus (HIV) P17/18 antibodies against α1 thymosin and of anti-α1 thymosin monoclonal antibody against P17/18 protein" Immunology Letters, 16, pp. 97–100 (1987).

Primary Examiner—Robert A. Wax
Assistant Examiner—R. Keith Baker
Attorney, Agent, or Firm—Elman Wilf & Fried

[57] ABSTRACT

Polypeptides in the size range 6–11 amino acids from discrete regions of the human immunodeficiency virus p17 protein are immunogenic and form the basis for diagnosis and therapy of HIV-related disease.

52 Claims, 6 Drawing Sheets

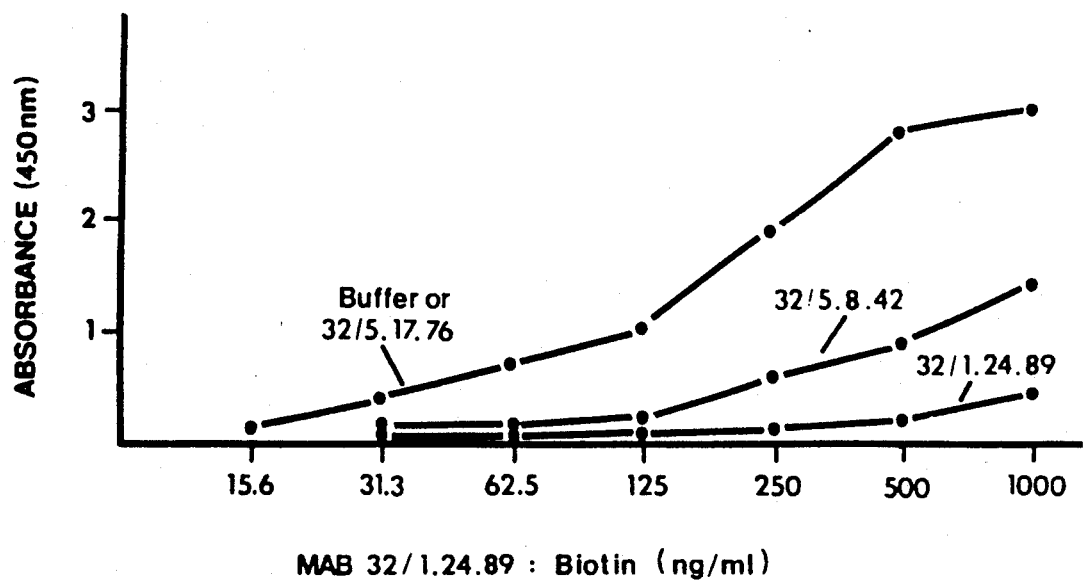
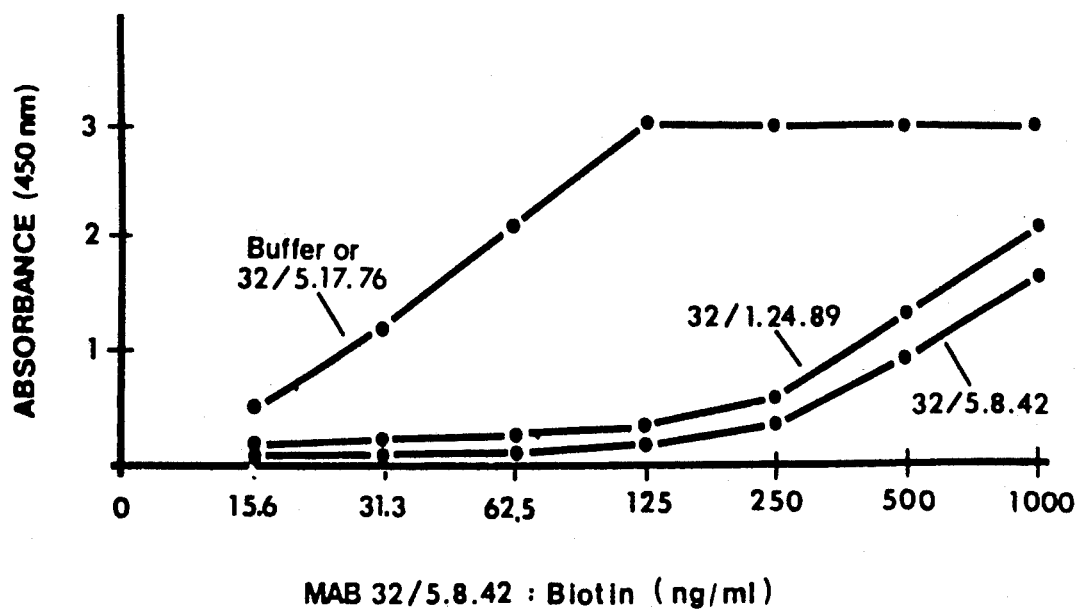
FIG. 4

SHORT POLYPEPTIDE SEQUENCES USEFUL IN THE PRODUCTION AND DETECTION OF ANTIBODIES AGAINST HUMAN IMMUNODEFICIENCY VIRUS

FIELD OF THE INVENTION

This invention relates to polypeptides useful in the therapy and diagnosis of diseases, especially acquired immunodeficiency disease (AIDS), for which human immunodeficiency virus (HIV) is the etiological agent.

BACKGROUND INFORMATION

Human Immunodeficiency Virus, type 1 (HIV) is the etiologic agent associated with acquired immunodeficiency syndrome (AIDS). It is lymphotropic for cells expressing the CD4 molecule.

In vitro infection by HIV can be blocked by serum antibodies obtained from infected individuals (1-3), although a precise relationship between antibody titers and disease course is not presently apparent. Several reports have also demonstrated that HIV-neutralizing antibodies can be developed against various immunogens, including glycoprotein extracts (4), recombinant proteins (5-6), and synthetic peptides (1, 7-8). These antibodies react with HIV env gene products, thus solidifying the role of viral surface glycoproteins and cell receptor interactions. In addition, antibodies to the CD4 molecule are capable of inhibiting viral binding activity, as are antiidiotypic reagents to these antibodies (9).

Although HIV envelope glycoproteins are of strong interest with respect to viral inhibition, recent information indicates that gag-encoded proteins may participate as a target for the neutralizing immune response. Gag encodes for a precursor protein of 55,000 molecular weight (p55) which is further degraded into three small proteins with molecular weights of approximately 17,000, 24,000 and 15,000 (p17, p24 and p15, respectively). These three proteins are termed the viral "core" proteins.

The present invention is related to polypeptides found in the p17 core protein of HIV. As demonstrated previously (17) the p17 core protein is comprised of 132 amino acids (more or less depending upon the strain of HIV examined) (FIG. 5), and residues at the 5' end of the gag gene of HIV and at the amino terminal portion of the p55 precursor protein. Certain regions of the p17 core protein (amino acid residues #88-115; TVAT . . . KKKA), exhibit homology with a peptide hormone produced by the human thymus termed thymosin alpha-1 (28). The same authors showed that antiserum to thymosin alpha-1 can neutralize the replication of HIV in vitro, as accounted for by the partial sequence homology between the hormone and the HIV p17 core protein. Further, heterologous antiserum to a 30-amino acid synthetic peptide analogue reacted with the p17 core protein of HIV in a manner identical to that seen with an HIV p17-specific antibody (12).

Previous work had resulted in the isolation of monoclonal antibodies against the p17 protein and the demonstration that those monoclonal antibodies could neutralize the virus. Nevertheless, the p17 protein is a relatively large entity of approximately 132 amino acids. The current invention reflects the discovery (described below in the Examples section) that certain short polypeptides, approximately 11 amino acids or even less in length, are the only ones that react with some monoclonal antibodies capable of neutralizing the biological activity of the HIV virus. The discovery that such short sequences exist and the identification of their structure allows one to construct proteins made exclusively or predominantly of antibody-reactive sequences and to use them as either diagnostic agents or inducers of anti-HIV antibodies. The resulting anti-HIV antibodies can, in turn be used to induce anti-idiotype antibodies themselves useful as antibody inducers.

The presently described immunoreactive polypeptides correspond to the following amino acids, numbered as to their position in the p17 protein (See FIG. 5 for the p17 sequence):

|  | Amino acid numbers in p17 |
| --- | --- |
| Polypeptide #1 | 12-19 |
| Polypeptide #1a | 12-17 |
| Polypeptide #1b | 13-18 |
| Polypeptide #1c | 14-19 |
| Polypeptide #2 | 17-22 |
| Polypeptide #3 | 12-22 |
| Polypeptide #4 | 100-105 |

When administered in the presence of adjuvants and/or carrier proteins, these peptides represent HIV vaccines of use to control or inhibit the spread of HIV contagion. In similar form, these peptides represent valuable immunogens with which to generate antibodies of use as diagnostic reagents. Alternatively, they can be used diagnostically to detect anti-HIV antibodies. Further, anti-HIV peptide antibodies are of use to develop anti-idiotype antibodies which themselves represent HIV vaccines when administered in the presence of appropriate adjuvants and/or carrier proteins.

Peptides #1, 1a, 1b, 1c, 2 and 3 represent sequences from the amino terminal region of the p17 HIV core protein. (i.e. the 5' region of the gag gene of HIV). Peptide #3 represents a combination of peptides #1, 1a, 1b and 2. Peptide #4 represents a region of the p17 core protein which bears some sequence homology to the thymic hormone, Thymosin alpha-1.

SUMMARY OF THE INVENTION

In its first aspect, the invention is a protein that comprises at least one polypeptide selected from the group consisting of Glu—Leu—Asp—Arg—Trp—Glu—Lys—Ile (SEQ ID NO: 1),
Glu—Leu—Asp—Arg—Trp—Glu (SEQ ID NO: 2),
Leu—Asp—Arg—Trp—Glu—Lys (SEQ ID NO: 3),
Asp—Arg—Trp—Glu—Lys—Ile (SEQ ID NO: 4),
Glu—Lys—Ile—Arg—Leu—Arg (SEQ ID NO: 5), and
Glu—Leu—Asp—Arg—Trp—Glu—Lys—Ile—Arg—Leu—Arg (SEQ ID NO: 6)

provided that said protein is not one found in a naturally occurring human immunodeficiency virus or other animal virus.

Another aspect of the invention is the use of protein that comprises at least one polypeptide selected from the group, consisting of Glu—Leu—Asp—Arg—Trp—Glu—Lys—Ile (SEQ ID NO: 1),
Glu—Leu—Asp—Arg—Trp—Glu (SEQ ID NO: 2),
Leu—Asp—Arg—Trp—Glu—Lys (SEQ ID NO: 3),
Asp—Arg—Trp—Glu—Lys—Ile (SEQ ID NO: 4),
Glu—Lys—Ile—Arg—Leu—Arg (SEQ ID NO: 5), and
Glu—Leu—Asp—Arg—Trp—Glu—Lys—Ile—Arg—Leu—Arg (SEQ ID NO: 6)

as an immunogen or vaccine in order to produce either antibodies with reactivity against a portion of human immunodeficiency virus (HIV) or cells capable of producing said antibodies provided said protein is not part of naturally occurring HIV or other animal virus.

Still another aspect of the invention is the use of protein that comprises at least one polypeptide selected from the group consisting of Glu—Leu—Asp—Arg—Trp—Glu—Lys—Ile (SEQ ID NO: 1),
Glu—Leu—Asp—Arg—Trp—Glu (SEQ ID NO: 2),
Leu—Asp—Arg—Trp—Glu—Lys (SEQ ID NO: 3),
Asp—Arg—Trp—Glu—Lys—Ile (SEQ ID NO: 4),
Glu—Lys—Ile—Arg—Leu—Arg (SEQ ID NO: 5), and
Glu—Leu—Asp—Arg—Trp—Glu—Lys—Ile—Arg—Leu—Arg (SEQ ID NO: 6)

to detect the presence in an animal of entities (such as antibodies) that will bind to said polypeptide or polypeptides providing said protein is not part of naturally occurring human immunodeficiency virus or other animal virus.

A related invention is the process of making a monoclonal antibody with specificity against a portion of HIV which comprises injecting an animal with a protein that contains at least one polypeptide selected from the group consisting of Glu—Leu—Asp—Arg—Trp—Glu—Lys—Ile (SEQ ID NO: 1),
Glu—Leu—Asp—Arg—Trp—Glu (SEQ ID NO: 2),
Leu—Asp—Arg—Trp—Glu—Lys (SEQ ID NO: 3),
Asp—Arg—Trp—Glu—Lys—Ile (SEQ ID NO: 4),
Glu—Lys—Ile—Arg—Leu—Arg (SEQ ID NO: 5), and
Glu—Leu—Asp—Arg—Trp—Glu—Lys—Ile—Arg—Leu—Arg (SEQ ID NO: 6)

isolating a spleen lymphocyte that makes the antibodies with specificity against the selected polypeptide, fusing that lymphocyte with a myeloma or other self-perpetuating cell to make a hybridoma and culturing the hybridoma under conditions where the desired monoclonal antibody is produced, provided said protein is not part of naturally occurring HIV or other animal virus. The invention is also the process of making anti-idiotypic monoclonal antibodies with specificity against anti-human immunodeficiency virus antibodies which comprises the aforesaid process of making monoclonal antibodies against a portion of HIV and the subsequent steps of injecting an animal with the anti-HIV monoclonal antibody, selecting a spleen lymphocyte that makes antibodies with the desired specificity, fusing the spleen lymphocyte with a myeloma or other self-perpetuating cell to make a hybridoma and culturing the hybridoma under conditions where the desired anti-idiotypic monoclonal antibody is produced.

Another process aspect of the invention is the process of inducing immunity against HIV which comprises injecting a human with a protein which comprises at least one polypeptide selected from the group consisting of Glu—Leu—Asp—Arg—Trp—Glu—Lys—Ile (SEQ ID NO: 1),
Glu—Leu—Asp—Arg—Trp—Glu (SEQ ID NO: 2),
Leu—Asp—Arg—Trp—Glu—Lys (SEQ ID NO: 3),
Asp—Arg—Trp—Glu—Lys—Ile (SEQ ID NO: 4),
Glu—Lys—Ile—Arg—Leu—Arg (SEQ ID NO: 5), and
Glu—Leu—Asp—Arg—Trp—Glu—Lys—Ile—Arg—Leu—Arg (SEQ ID NO: 6)

provided said protein is not part of naturally occurring HIV or other animal virus. Closely related is the invention that is the process of inducing immunity against HIV which comprises injecting a human with a monoclonal antibody made by the aforementioned process of making a monoclonal antibody against HIV.

Another aspect of the invention is the process of reacting a protein that comprises at least one polypeptide selected from the group consisting of Glu—Leu—Asp—Arg—Trp—Glu—Lys—Ile (SEQ ID NO: 1),
Glu—Leu—Asp—Arg—Trp—Glu (SEQ ID NO: 2),
Leu—Asp—Arg—Trp—Glu—Lys (SEQ ID NO: 3),
Asp—Arg—Trp—Glu—Lys—Ile (SEQ ID NO: 4),
Glu—Lys—Ile—Arg—Leu—Arg (SEQ ID NO: 5), and
Glu—Leu—Asp—Arg—Trp—Glu—Lys—Ile—Arg—Leu—Arg (SEQ ID NO: 6)

with an antibody or blood cell provided said protein is not part of naturally occurring (HIV) or other animal virus.

Another aspect of the invention is a monoclonal antibody made from a hybridoma crating by cell fusion of a myeloma or other self-perpetuating cell with a spleen lymphocyte isolated from an animal exposed to a protein comprising at least one polypeptide selected from the group consisting of Glu—Leu—Asp—Arg—Trp—Glu—Lys—Ile (SEQ ID NO: 1),
Glu—Leu—Asp—Arg—Trp—Glu (SEQ ID NO: 2),
Leu—Asp—Arg—Trp—Glu—Lys (SEQ ID NO: 3),
Asp—Arg—Trp—Glu—Lys—Ile (SEQ ID NO: 4),
Glu—Lys—Ile—Arg—Leu—Arg (SEQ ID NO: 5), and
Glu—Leu—Asp—Arg—Trp—Glu—Lys—Ile—Arg—Leu—Arg (SEQ ID NO: 6)

said monoclonal antibodies being reactive with said selected polypeptide, provided said protein is not part of naturally occurring HIV or other animal virus. The resulting antibody is part of the definition of a related aspect of the invention: a monoclonal anti-idiotypic antibody made from a hybridoma created by cell fusion of a myeloma or other self-perpetuating cell with a spleen lymphocyte isolated from an animal exposed to said resulting monoclonal antibody. The resulting anti-idiotype antibody is part of the definition of a further related aspect of the invention: An anti-anti-idiotypic antibody generated as a result of using a said resulting anti-idiotype antibody as an immunogen or vaccine.

In all of the above inventions involving a protein that comprises at least one polypeptide selected from the group consisting of Glu—Leu—Asp—Arg—Trp—Glu—Lys—Ile (SEQ ID NO: 1),
Glu—Leu—Asp—Arg—Trp—Glu (SEQ ID NO: 2),
Leu—Asp—Arg—Trp—Glu—Lys (SEQ ID NO: 3),
Asp—Arg—Trp—Glu—Lys—Ile (SEQ ID NO: 4),
Glu—Lys—Ile—Arg—Leu—Arg (SEQ ID NO: 5), and
Glu—Leu—Asp—Arg—Trp—Glu—Lys—Ile—Arg—Leu—Arg (SEQ ID NO: 6)

provided said protein is not part of naturally occurring HIV or other animal virus, there are subgeneric aspects to the invention, wherein:

(1) the protein comprises a multimer of either

Glu—Leu—Asp—Arg—Trp—Glu—Lys—Ile (SEQ ID NO: 1),
Glu—Leu—Asp—Arg—Trp—Glu (SEQ ID NO: 2),
Leu—Asp—Arg—Trp—Glu—Lys (SEQ ID NO: 3),
Asp—Arg—Trp—Glu—Lys—Ile (SEQ ID NO: 4),
Glu—Lys—Ile—Arg—Leu—Arg (SEQ ID NO: 5), and
Glu—Leu—Asp—Arg—Trp—Glu—Lys—Ile—Arg—Leu—Arg (SEQ ID NO: 6)

(2) the protein comprises a polymer of either

Glu—Leu—Asp—Arg—Trp—Glu—Lys—Ile (SEQ ID NO: 1),
Glu—Leu—Asp—Arg—Trp—Glu (SEQ ID NO: 2),
Leu—Asp—Arg—Trp—Glu—Lys (SEQ ID NO: 3),
Asp—Arg—Trp—Glu—Lys—Ile (SEQ ID NO: 4),
Glu—Lys—Ile—Arg—Leu—Arg (SEQ ID NO: 5), and
Glu—Leu—Asp—Arg—Trp—Glu—Lys—Ile—Arg—Leu—Arg (SEQ ID NO: 6)

(3) the protein is a multimer of either

Glu—Leu—Asp—Arg—Trp—Glu—Lys—Ile (SEQ ID NO: 1),
Glu—Leu—Asp—Arg—Trp—Glu (SEQ ID NO: 2),
Leu—Asp—Arg—Trp—Glu—Lys (SEQ ID NO: 3),
Asp—Arg—Trp—Glu—Lys—Ile (SEQ ID NO: 4),
Glu—Lys—Ile—Arg—Leu—Arg (SEQ ID NO: 5), and
Glu—Leu—Asp—Arg—Trp—Glu—Lys—Ile—Arg—Leu—Arg (SEQ ID NO: 6)

(4) the protein is a polymer of either

Glu—Leu—Asp—Arg—Trp—Glu—Lys—Ile (SEQ ID NO: 1),
Glu—Leu—Asp—Arg—Trp—Glu (SEQ ID NO: 2),
Leu—Asp—Arg—Trp—Glu—Lys (SEQ ID NO: 3),
Asp—Arg—Trp—Glu—Lys—Ile (SEQ ID NO: 4),
Glu—Lys—Ile—Arg—Leu—Arg (SEQ ID NO: 5), and
Glu—Leu—Asp—Arg—Trp—Glu—Lys—Ile—Arg—Leu—Arg (SEQ ID NO: 6)

(5) the protein has at least two copies of one polypeptide selected from the group Glu—Leu—Asp—Arg—Trp—Glu—Lys—Ile (SEQ ID NO: 1),
Glu—Leu—Asp—Arg—Trp—Glu (SEQ ID NO: 2),
Leu—Asp—Arg—Trp—Glu—Lys (SEQ ID NO: 3),
Asp—Arg—Trp—Glu—Lys—Ile (SEQ ID NO: 4),
Glu—Lys—Ile—Arg—Leu—Arg (SEQ ID NO: 5), and
Glu—Leu—Asp—Arg—Trp—Glu—Lys—Ile—Arg—Leu—Arg (SEQ ID NO: 6)

but does not comprise a multimer of that polypeptide or polymer of that polypeptide.

BRIEF DESCRIPTION OF THE DRAWINGS

FIG. 1. Reactivity of HIV with monoclonal antibodies as determined using Western blot analysis. (lane A), HIV-seropositive human serum #H-731 diluted 1/1000; (lane B) monoclonal anti-p17 antibody, clone 32/5.8.42;

(lane C), monoclonal anti-p17 antibody, clone 32/1.24.89; (lane D), monoclonal anti-gp160 antibody, clone 10E9; (lane E), monoclonal anti-p24 antibody, clone 32.5.17.76; (lane F) control, IgG-subclass monoclonal antibody, clone F5 (anti-prostate antibody, ref. 26).

FIG. 2. Inhibition of the cell-free HIV infectivity of HUT-102 cells by monoclonal anti-p17 antibodies. HUT-102 cells were challenged with $10^3$ TCID$_{50}$ units of HIV in the presence of antibodies as described in Materials and Methods. Reverse transcriptase measurements were taken at 10 days post-infection. Abscissa, concentration of control or experimental antibodies; ordinate, reverse transcriptase activity (mean of triplicates) as a percentage of positive control cultures (virus only, no inhibitor). HIV+, IgG fraction of seropositive human serum; HIV− IgG fraction of seronegative human serum.

Results shown are the mean and s.e.m. of two separate experiments. Control reverse transcriptase levels (cpm) were $2.6 \times 10^6$ (experiment #1) and $1.6 \times 10^6$ (experiment #2).

FIG. 3. Neutralization of the cell-free HIV infectivity of T-lymphocytes by monoclonal antibodies. Normal donor peripheral blood mononuculear cells were pre-stimulated with PHA/IL-2 as described in Materials and Methods, washed and challenged with $10^3$ TCID$_{50}$ doses of HIV in the presence of antibodies or control immunoglobulins. After ten days, viral replication was measured by reverse transcriptase measurements. Same antibodies as in FIG. 2. Control reverse transcriptase (cpm), $3.5 \times 10^5$.

FIG. 4. Reciprocal, competitive binding inhibition analysis of monoclonal anti-p17 antibodies. Increasing concentrations of biotin-antibodies (abscissa) were allowed to react with solid-phase HIV in the absence or presence of competing antibodies, each at 5 ug/ml. Thereafter, the reactions were developed using streptavidin-peroxidase, substrate, and absorbance was measured at 450 nm (ordinate). Results were expressed as optical density versus input level of biotin-labeled monoclonal antibody in the presence of absence of inhibitors.

Top: reactivity of biotin-labeled monoclonal anti-p17 antibody, clone 32/1.24.89.
  Bottom: reactivity of biotin-labeled anti-p17 antibody, clone 32/5.8.42.
  Buffer, no inhibitor; 32/5.17.76, anti-p24 monoclonal antibody.

FIG. 5. Epitope mapping of monoclonal antibodies to p17 using epitope scanning (Geysen technique). A series of sequential, overlapping hexapeptides were synthesized in situ on solid phase pins, as described in Materials and Methods. The peptide series corresponds to the entire HIV p17 reading frame, beginning at the ATG (met) start codon. The peptides were probed for immunoreactivity against monoclonal anti-p17 antibodies (clones 32/5.8.42 and 32/1.24.89) at 10 ug/ml. The reactions were developed using biotin-labeled goat antibodies to murine IgG followed by streptavidin-peroxidase and then substrate. Results are expressed as optical density (ordinate) versus peptide number (abscissa).
  Control monoclonal antibodies F5 (26) and 32/5.17.76 (anti-p24) demonstrated no reactivity versus any peptide (not shown).

FIG. 6. Competitive inhibition of monoclonal anti-p17 antibodies by soluble, synthetic peptides. Peptides were synthesized which corresponded to the antibody-reactive epitopes identified using epitope scanning (FIG. 5). Increasing concentrations of soluble peptides (abscissa) were allowed to compete for the reaction of monoclonal antibodies versus HIV target antigen. The reactions were developed using biotin-avidin enzyme reagents and then substrate.

SP-17-A, synthetic peptide corresponding to the reactive site of monoclonal anti-p17 antibody clone 32/5.8.42. (Glu Leu Asp Arg Trp Glu Lys Ile) (SEQ ID NO:1).
  SP-17-B, synthetic peptide corresponding to the reactive site of monoclonal anti-p17 antibody clone 32/1.24.89. (Glu Lys Ile Arg Leu Arg) (SEQ ID NO:5).
  SP-17-A/B, synthetic peptide containing both antibody-reactive sites above. (Glu Leu Asp Arg Trp Glu Lys Ile Arg Leu Arg) (SEQ ID NO:6).

MAb 32/5.8.42

MAb 32/1.24.89

The concentrations of peptides which produced a 50% inhibition of antibody binding activity (ID$_{50}$) are indicated in the Figure.

DETAILED DESCRIPTION

Definitions

Figure 1:
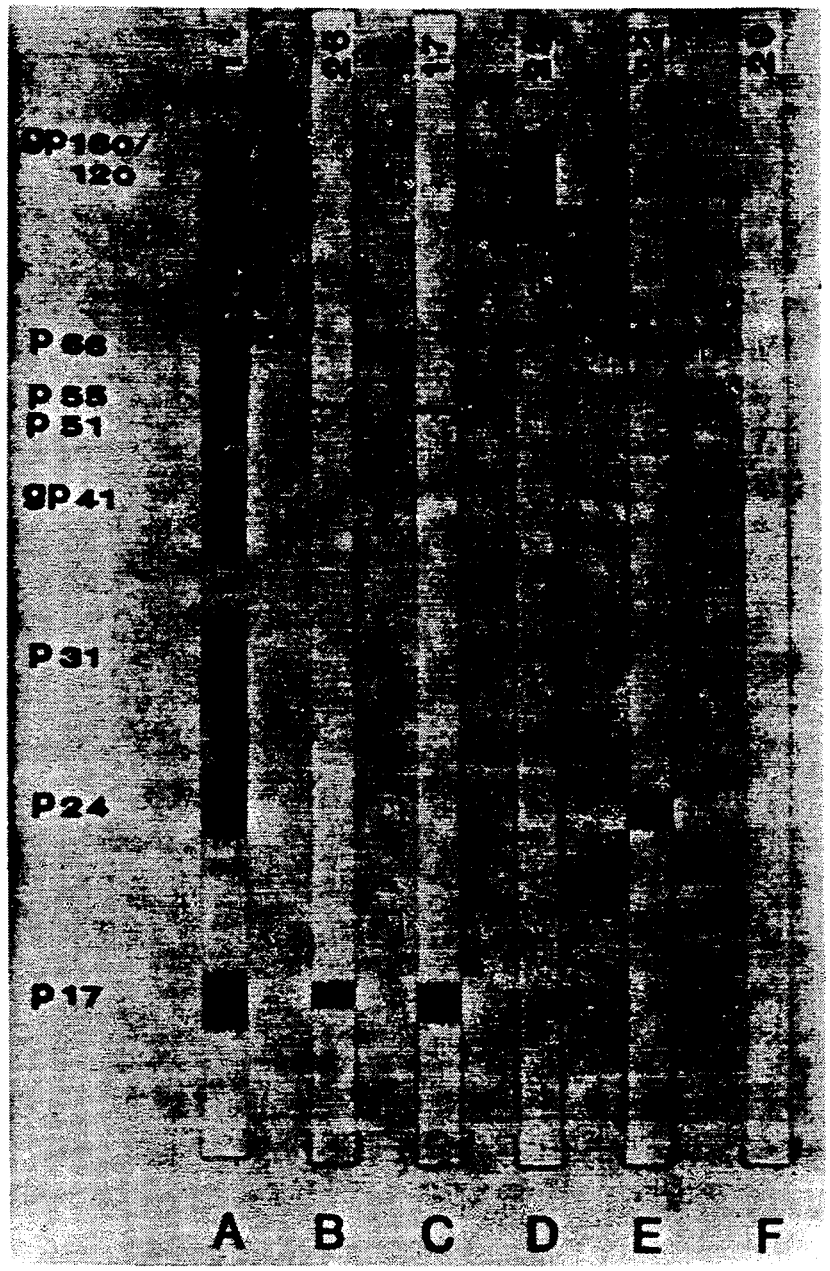

A "substantially pure" preparation of a protein is one that has the purity achievable by normal chemical or biochemical procedures, such as the ones described herein, and is to be distinguished from a "natural" preparation of a protein, such as a protein that is part of a virus, a living cell, or a mammal or other animal, and is therefore in close proximity with other species of biochemical molecules.

All amino acids identified herein are in the natural or L-configuration. In keeping with standard nomeclature, abbreviations for amino acid residues are as follows:

| 1-LETTER SYMBOL | 3-LETTER SYMBOL | AMINO ACID |
|---|---|---|
| A | Ala | L-alanine |
| C | Cys | L-cysteine |
| D | Asp | L-aspartic acid |
| E | Glu | L-glutamic acid |
| F | Phe | L-phenylalanine |
| G | Gly | L-glycine |
| H | His | L-histidine |
| I | Ile | L-isoleucine |
| K | Lys | L-lysine |
| L | Leu | L-leucine |
| M | Met | L-methionine |
| N | Asn | L-asparagine |
| P | Pro | L-proline |
| Q | Gln | L-glutamine |
| R | Arg | L-arginine |
| S | Ser | L-serine |
| T | Thr | L-threonine |
| V | Val | L-valine |
| W | Trp | L-tryptophan |
| Y | Tyr | L-tyrosine |

Sequences defined by formula (e.g., Glu-Leu-Asp-Arg-Trp-Glu-Lys-Ile) (SEQ ID NO:1) are, left to right, in the direction of amino terminus to carboxy terminus.

The polypeptides of this invention are also referred to herein simply as "peptides".

The term "antigenically related variants" is used to designate polypeptides of differing overall amino acid residue sequence that share at least a portion of one antigenic determinant and are therefore immunologically cross-reactive.

The term "antigenic determinant", designates the structural component of a molecule that is responsible for specific interaction with corresponding antibody (immunoglobulin) molecules elicited by the same or related antigen or immunogen.

The term "immunogenic determinant", as used herein, designates the structural component of a molecule that is responsible for the induction in a host of an antibody containing an antibody combining site (idiotype) that binds with the immunogen when used as an antigen.

The term "antigen", as used herein, means an entity that is bound by an antibody.

The term "immunogen", as used herein, describes an entity that induces antibody production in the host animal. In some instances, the antigen and immunogen are the same entity, while in other instances, the two entities are different.

The word "inoculum" is used herein to describe a composition containing a polypeptide of this invention as an active ingredient used for the preparation of antibodies against HIV. When a polypeptide is used to induce antibodies it is to be understood that the polypeptide may be used alone, or linked to a carrier.

The word "vaccine" is used herein to described a type of inoculum containing a polypeptide of this invention as an active ingredient that is used to induce active immunity in a host mammal.

The phrase "pharmaceutically acceptable salts", as used herein, refers to non-toxic alkali metal, alkaline earth metal and ammonium salts used in the pharmaceutical industry, including the sodium, potassium lithium, calcium, magnesium and ammonium salts and the like that are prepared by methods well-known in the art. The phrase also includes non-toxic acid addition salts that are generally prepared by reacting components of this invention with a suitable organic or inorganic acid. Representative salts include the hydrochloride, hydrobromide, sulfate, bisulfate, acetate, oxalate, valerate, oleate, laurate, vorate, benzoate, lactate, phosphate, tosylate, citrate, maleate, fumarate, succinate, tartrate, and the like.

A "multimer" is a chain of two or more identical polypeptides joined in a head-to-tail manner by peptide bonds. A multimer may either represent the entire structure of a protein or represent part of the structure of a protein.

A "polymer" is a molecule that contains a two or more polypeptides joined together by bonds other than peptide bonds. A polymer may represent the entire structure of a protein or represent part of the structure of a protein.

The word "protein" is understood to include multimers and polymers.

The term "unit dose" refers to physically discrete units suitable as unitary dosages for animals, each unit containing a predetermined quantity of active material calculated to produce the desired therapeutic effect in association with the required diluent; i.e., carrier, or vehicle. The specifications for the novel unit dose of this invention are dictated by and are directly dependent on the unique characteristics of the active material and the particular therapeutic effect to be achieved.

Embodiments of the Invention

Embodiments of the present invention include the proteins of the invention described herein, the pharmaceutically acceptable salts thereof, and antigenically related variants thereof. Each of the embodiments is capable of inducing, in humans, rabbits and mice, antibodies that bind to the protein of the invention represented in that embodiment.

The polypeptides of this invention can be part of proteins whose structure includes other polypeptides yet still retain their immunogenic properties.

The present invention also contemplates a multimer containing at least two joined synthetic polypeptide repeating units wherein at least one of the repeating units is a polypeptide as described within.

The multimers of this invention, alone or linked to a carrier, when introduced in an effective amount into a host, are capable of inducing the production of antibodies that bind to HIV.

Thus, the multimers of this invention, like the polypeptide, are immunogenic. Those multimers may therefore be used to induce the production of anti-HIV antibodies that are useful in the diagnostic methods and systems discussed hereinafter, and may also be used as an antigen in appropriate diagnostic methods and systems.

Multimers that contain fewer than about 35 amino acid residues in the total multimer are typically linked to a carrier for use as an immunogen. Those multimers that contain more than a total of about 35 amino acid residues are typically sufficiently immunogenic to be used without a carrier.

Polypeptide multimers may be prepared by bonding together the synthesized polypeptide monomers in a head-to-tail manner using the aforementioned solid phase method; i.e., one complete polypeptide sequence can be synthesized on the resin, followed by one or more of the same or different polypeptide sequences, with the entire multimeric unit thereafter being cleaved from the resin and used as described herein. Such head-to-tail polypeptide multimers preferably contain about 2 to 4 polypeptide repeating units.

An exemplary polymer of this invention can be synthesized using a polypeptide of this invention that contains added cysteine residues at both the amino- and carboxy-termini (diCys polypeptide). The diCys polypeptide may be bonded together by intramolecular, interpolypeptide cysteine disulfide bonds utilizing an oxidation procedure to form an immunogenic, antigenic polymer. The polymer so prepared contains two or more polypeptides of this invention as repeating units. Those repeating units are bonded together by the above-discussed oxidized cysteine (cystine) residues.

The presence of one or two terminal Cys residues in a polypeptide of this invention for the purposes of binding the polypeptide to a carrier or for preparing a polymer is not to be construed as altering the amino acid sequence of polypeptide repeating units of this invention.

The polypeptides of this invention are used in a pharmaceutically acceptable diluent to form an inoculum or a vaccine that, when administered in an effective amount, is capable of inducing antibodies that immunoreact with HIV.

For polypeptides that contain fewer than about 35 amino acid residues, it is preferable to use a carrier for the purpose of inducing the production of antibodies.

Active immunity involves the production of antibodies. Thus, a vaccine or inoculum may contain identical ingredients through their uses are different. Alternatively, in some cases, the ingredients of a vaccine and of an inoculum are different because many adjuvants useful in animals may not be used in humans.

The present inoculum or vaccine contains an effective amount of a polypeptide of this invention. The effective amount of polypeptide per unit dose depends, among other things, on the species of animal inoculated, the body weight of the animal and the chosen inoculation regimen as is well known in the art. Inocula and vaccines typically contain polypeptide concentrations of about 100 micrograms to about 500 milligrams per inoculation (dose). The stated amounts of polypeptide refer to the weight of polypeptide without the weight of a carrier, when a carrier is used. Specific, exemplary inocula are described hereinafter with weight of carrier plus polypeptide (conjugate) being given.

Antibodies and substantially whole antibodies raised to (induced by) the polypeptides of this invention as well as antibody combining sites prepared from such antibodies constitute still another embodiment of this invention. Antibodies are raised in mammalian hosts such as mice, guinea pigs, rabbits, hoses and the like by immunization using the inocula described hereinabove.

Monoclonal antibodies need not only be obtained from hybridoma supernatants, but may also be obtained in generally more concentrated form from ascites fluid of mammals into which the desired hybridoma has been introduced. Production of monoclonal antibodies using ascites fluid is well known and will not be dealt with further herein.

An antibody of this invention binds both to the polypeptide to which it was raised and also binds to the corresponding HIV antigenic determinant site that the polypeptide of this invention immunologically mimics. Thus, a polypeptide of this invention may be both an immunogen and an antigen.

The antibodies of this invention may be described as being oligoclonal as compared to naturally occurring polyclonal antibodies since they are raised to an immunogen having relatively few epitopes as compared to the epitopes of an intact HIV antigenic molecule. Consequently, antibodies of this invention bind to epitopes of the polypeptide while naturally occurring antibodies raised to antigens of HIV bind to epitopes throughout the HIV antigenic molecule.

The polypeptides, antibodies and antibody combining sites raised to the before described polypeptides, and methods of the present invention may also be used for diagnostic test, such as immunoassys. Such diagnostic techniques include, for example, enzyme immune assay, enzyme multiplied immunoassay technique (EMIT), enzyme-linked immunosorbent (ELISA), radio-immune assay (RIA), fluorescence immune assay, either single or double antibody techniques, and other techniques in which either the receptor or the antigen is labeled with some detectable tag or indicating means. See generally Maggio, Enzyme Immunoassay, CRC Press, Cleveland, Ohio (1981); and Goldman, M., Fluorescent Antibody Methods, Academic Press, New York, N.Y. (1980).

Vaccines can also be produced using antibodies which are immunologically specific to the anti-peptide antibodies described above. These "anti-antibodies" are termed anti-idiotypic antibodies (anti-ids) and may be monoclonal or polyclonal in nature. Such approaches to vaccine construction have been reviewed before (29) and are described in the Materials and Methods section.

Synthesis of Polypeptides

The polypeptides of this invention are chemically synthesized by solid-phase methods as previously described (18, 30) [See also U.S. Pat. No. 4,316,891, issued to Guillemin et al.] The solid phase method of polypeptide synthesis is practiced utilizing a Beckman Model 990B Polypeptide Synthesizer, available commercially from Beckman Instrument Co., Berkeley, Calif., or an equivalent instrument.

For polypeptides having fewer than 35 residues that are used in inocula, a cysteine residue is added to the carboxy-terminus or the amino-terminus or both the amino-terminus and the carboxy-terminus to assist in coupling to a protein carrier as described below. The compositions of all polypeptides are confirmed by amino acid analysis.

In preparing a synthetic polypeptide of this invention by the above solid phase method, the amino acid residues are linked to a resin (solid phase) through an ester linkage from the carboxy-terminal residue. When the polypeptide is to be linked to a carrier via a Cys residue or polymerized via terminal Cys residues, it is convenient to utilize that Cys residue as the carboxy-terminal residue that is ester-bonded to the resin.

The alpha-amino group of each added amino acid is typically protected by a tertiary-butoxcarbonyl (t-BOC) group prior to the amino acid being added into the growing polypeptide chain. The t-BOC group is then removed prior to addition of the next amino acid to the growing polypeptide chain.

Reactive amino acid side chains are also protected during synthesis of the polypeptides. Usual side-chain protecting groups used for the remaining amino acid residues are as follows: O-(bromobenzyloxycarbonyl) for tyrosine; O-benzyl for threonine, serine, aspartic acid and glutamic acid; S-methoxybenzyl for cysteine, dinitrophenyl for histidine; 2-chlorobenzoxycarbonyl for lysine and tosyl for arginine.

Protected amino acids are recrystallized from appropriate solvents to give single spots by thin layer chromatography. Couplings are typically carried out using a ten-fold molar excess of both protected amino acid and dicyclohexyl carbodiimide over the number of milliequivalents of initial N-terminal amino acid. A two molar excess of both reagents may also be used. For asparagine, an equal molar amount of N-hydroxy-benzotriazole is added to the protected amino acid and dimethyl formamide is used as the solvent.

After preparation of a desired polypeptide, a portion of the resulting, protected polypeptide (about 1 gram) is treated with two milliliters of anisole, and anhydrous hydrogen fluoride, about 20 milliliters, is condensed into the reaction vessel at dry ice temperature. The resulting mixture is stirred at about 4 degrees C., for about one hour to cleave the protecting groups and to remove the polypeptide from the resin. After evaporating the hydrogen fluoride at a temperature of 4 degrees C., with a stream of N2, the residue is extracted with anhydrous diethyl ether three times to remove the anisole, and the residue is dried in vacuo.

The vacuum dried material is extracted with 5% aqueous acetic acid (3 times with 50 milliliters) to separate the free polypeptide from the resin. The extract-containing solution is lyophilized to provide a monomeric unoxidized polypeptide.

The produced synthetic polypeptide may be used as a reagent in an enzyme-linked immumosorbent assay (ELISA) to detect anti-HIV antibodies. The synthetic polypeptide may also be used to produce an inoculum, usually by linking it to a carrier to form conjugate and then dispersing an effective amount of the conjugate in a physiologically tolerable diluent, as is discussed hereinafter.

It is also to be noted that a synthetic multimer of this invention can be prepared by the solid phase, synthesis of a plurality of the polypeptides of this invention linked together end-to-end (head-to-tail) by an amide bond between the carboxyl-terminal residue of one polypeptide and the amino-terminal residue of a second polypeptide "peptide bond". Such synthetic multimers are preferably synthesized as a single long polypeptide multimer, but can also be prepared as individual polypeptides that are linked together subsequent to their individual synthesis, using a carbodiimide reagent such as 1-(3-dimethylaminopropyl)-3-ethyl-carbodiimide hydrochloride in water. The total number of amino acid residues contained in a multimer prepared as a single polypeptide chain is preferably less than about 50. A synthetic head-to-tail multimer more preferably contains two to about four blocks of linked, synthetic, random copolymer polypeptides of this invention, and a total of less than about 40 amino acid residues.

Preparation of Polymers

The polypeptides of the present invention may be connected together to form an antigenic and/or immunogenic polymer comprising a plurality of the polypeptide repeating units. Such a polymer typically has the advantage of increased immunogenicity and antigenicity. In addition, a carrier is typically not needed when a polymeric immunogen is utilized. Where different polypeptide monomers are used to make up the polymer, the ability to immunoreact with antibodies to several HIV antigenic determinants is obtained. A still further advantage is the ability of such a polymer when used in an inoculum to induce antibodies that immunoreact with several antigenic determinants of a HIV antigen.

A polymer of this invention may be prepared by synthesizing the polypeptides as discussed above and including cysteine residues at both amino- and carboxy-termini to form a "diCys-terminated" polypeptide. After synthesis, in a typical laboratory preparation, 10 milligrams of the diCys polypeptide (containing cysteine residues in un-oxidized form) are dissolved in 250 milliliters (ml) of 0.1 molar (M) ammonium bicarbonate buffer. The dissolved diCys-terminated polypeptide is then air oxidized by stirring the resulting solution gently for a period of about 18 hours in the air, or until there is no detectable free mercaptan by the Ellman test [See (31)]

The polymer so prepared contains a plurality of the synthetic, random copolymer polypeptide repeating units that are bonded together by oxidizing cysteine (cystine) residues. Such polymers typically contain their polypeptide repeating units bonded together in a head-to-tail manner as well as in head-to-head and tail-to-tail manners; i.e., the amino-termini of two polypeptide repeating units may be bonded together through a a single cystine residue as may two carboxyl-termini since the linking groups at both polypeptide termini are identical.

Coupling to Carriers

The synthetic polypeptides are coupled to keyhole limpet hemocyanin (KLH) as carrier by the method described in (32). Briefly, 4 milligrams (mg) of the carrier are activated with 0.51 mg of m-maleimidobenzoyl-N-hydroxysuccinimide ester and subsequently reacted with 5 mg of the polypeptide through an amino- or carboxy-terminal cysteine to provide a conjugate containing about 10 to about 35 percent by weight polypeptide.

One or more additional amino acid residues may be added to the amino- or carboxy-termini of the synthetic polypeptide to assist in binding the polypeptide to a carrier. Cysteine residues have been found to be particularly useful for forming polymers via disulfide bonds. However, other methods well known in the art for preparing conjugates can also be used. Exemplary additional linking procedures include the use of Michael addition reaction products, dialdehydes such as glutaraldehyde [See (33)], and the like, or the use of carbodiimide technology as in the use of a water-soluble carbodiimide to form amide links to the carrier, as discussed before for linking a plurality of polypeptides together to form a synthetic multimer.

Useful carriers are well known in the art, and are generally proteins themselves. Exemplary of such carriers are keyhole hemocyanin (KLH), edestin, thyroglobulin, albumins such as bovine serum albumin (BSA) or human serum albumin (HSA), red blood cells such as sheep erythrocytes (SRBC), tetanus toxoid, cholera toxoid as well as polyamino acid such as poly (D-lysine:D-glutaminic acid), and the like.

As is also well known in the art, it is often beneficial to bind a synthetic polypeptide to its carrier by means of an intermediate, linking group. As noted above, glutaraldehyde is one such linking group. However, when cysteine is used, the intermediate linking group is preferably an m-maleimidobenxoyl N-hydroxy succinimide (MBS) as was used herein.

Additionally, MBS may be first added to the carrier by an ester-amide interchange reaction as disclosed by Lie et al., supra. Thereafter, the addition can be followed by addition of a blocked mercapto group such as thiolacetic acid (CH3COSH) across the maleimido-double bond. After cleavage of the acyl blocking group, a disulfide bond is formed between the deblocked linking group mercaptan and the mercaptan of the added cysteine residue of the synthetic polypeptide.

The choice of carrier is more dependent upon the ultimate use of the immunogen than upon the determinant portion of the immunogen, and is based upon criteria not particularly involved in the present invention. For example, if a inoculum is to be used in animals, a carrier that does not generate an untoward reaction in the particular animal should be selected.

ELISA

Anti-polypeptide antibody binding and inhibition studies may be prepared by an enzyme-linked immunosorbent assay (ELISA) as described below.

Briefly, microtiter wells (Costar, #3590, Cambridge, Mass.) are coated with individual polypeptides as antigens by adding 100 microliters (ul) of BBS [10 millimoler (mM) sodium borate (pH 8.3), 150 mM NaCl] containing polypeptide at a concentration of 10 micrograms per milliliter (ug/ml). Contact between the wells and antigen-containing solution is maintained for a predetermined time, typically 1–18 hr., and at 20 degrees C., to form an antigen-coated solid phase. The solid and liquid phases are separated and the wells are washed three times with BBS.

Non-specific binding sites are blocked by admixing 200 microliters of 1 percent bovine serum albumin (BSA) in each well to form another solid-liquid phase admixture, and maintaining the solid-liquid phase admixture for approximately 30 minutes, at 20 degrees C. The phases are separated and excess, unbound BSA is removed by washing three times with BBS.

Rabbit (or guinea pig) and human sera (body sample aliquots) are assayed for anti-polypeptide activity by adding 100 microliters of serum diluted 1:20 in BBS per well to form a solid/liquid phase composition. Contact between the diluted sera and the antigen-coated solid phase is maintained for a predetermined time such as 1 hour, and at 20 degrees C., for an immunoreactant to form. The solid and liquid phases are separated, and the solid phase; i.e., antigen-coated, immunoreactant containing wells, is then washed three time with BBS.

The antibodies in human sera that immunoreact with an adsorbed polypeptide may be detected using an indicating means comprising alkaline phosphatase-conjugated goat anti-human Ig antibody (Tago, Burlington, Calif.). The antibodies in rabbit sera that immunoreact with an adsorbed polypeptide may be detected using an indicating means comprising alkaline phosphatase-conjugated goat anti-rabbit Ig antibody (Kirkegard & Perry Laboratories, Inc., Gaithersburg, Md.). In either instance, 100 microliters of the indicating antibody diluted 1:300 in BBS are added per well to form a further solid-liquid phase composition. This solid-liquid phase composition is maintained for a predetermined time, one hour, for the formation of a reaction product between the human antibodies bound to the solid phase and the indicating means, and at 20 degrees C. The phases are separated, and the solid phase is washed 3 washed with BBS.

Alkaline phosphatase-conjugated antibody bound to polypeptide specific antibody may be detected by spectrophotometrically measuring the enzymatic hydrolysis of p-nitrophenyl phosphate to p-nitrophenol. Briefly, 100 microliters of p-nitrophenyl phosphate [1 milligram per milliliter in 2 mM magnesium chloride (pH 9.8), 50 mM sodium carbonate] are added to each well. The enzymatic reaction is allowed to proceed 1 hour and then the optical density at 405 nm is determined in a TITERTEK spectrophotometer available from FLOW Laboratories, Inglewood, Calif.

Immunizations

Antibodies of this invention include whole antibodies raised in mammals by immunizing them with inocula including a polypeptide and/or multimer as describer hereinabove. Both polypeptides and multimers may be used included in inocula alone or conjugated to a carrier protein such as keyhole limpet hemocyamin (KLH). However, polypeptides are preferably used as a conjugate and multimers are preferably used alone.

Rabbits may be immunized with inocula containing 1.0 mg of conjugate in complete Freund's adjuvant (CFA), and boosted one month later with 1.0 mg of conjugate in incomplete Freund's adjuvant (IFA). Each immunization consistent of one subcutaneous injection, on the back hip. Rabbits are bled 1 and 2 months subsequent to the boost.

Individual inocula are prepared with CFA or IFA as follows: An amount of conjugate sufficient to provide the desired amount of polypeptide per inoculation (e.g., 1 mg) is dissolved in PBS (at about 0.5 ml) at pH 7.2. Equal volumes of CFA or IFA are then mixed with the conjugate solutions to provide an inoculum containing conjugate, water and adjuvant in which the water to oil ratio was 1:1. The mixture is thereafter homogenized to provide the inocula. The volume of an inoculum so prepared is typically greater than 1 ml, and some of the conjugate, PBS and adjuvant may be lost during the emulsification. Substantially all of the emulsion that can be recovered is placed into a syringe, and then is introduced into the rabbits as discussed before. The amount of inoculum introduced into the rabbits should be at least about 90 percent of that present prior to the emulsification step.

Sera containing immunologically active antibodies are produced from the bleeds by methods well known in the art. These anti-peptide antibodies are immunoreactive with one or more of the polypeptides of this invention, with HIV antigenic determinants and will also specifically neutralize HIV infectivity. The immunizations will also induce a cell-medicated immunity against peptides and HIV antigenic determinants, as commonly monitored by delayed-type hypersensitivity reaction.

Delayed Type Hypersensitivity Test (Skin Reaction Test)

The above inocula stock solutions are illustrative of the inocula of this invention. As demonstrated herein, they may be used to produce antibody molecules that immunoreact with HIV antigens.

The previously described diagnostic systems and assays are based on in vitro assays. Although particular steps of the assays can be carried out in vivo, the actual immune response is measured in tissue culture. The present invention, however, can also be applied to diagnostic systems involving the in vivo measurement of T cell responses. One example of such a system is a delayed-type cutaneous hypersensitivity (DCH) reaction or what is more commonly known as a skin reaction test.

A DCH reaction can only occur in an individual previously exposed (sensitized) to a given antigen. The first exposure of an individual to the antigen produces no visible change, but the immune status of the individual is altered in that hypersensitivity to renewed exposure to that antigen results. Thus, upon intradermal or subcutaneous injection of the antigen (preferably in a buffered saline solution) a characteristic skin lesion develops at the injection site-a lesion that would not develop after a first antigen exposure. Because the response to the second (or challenge) antigen inoculum is typically delayed by 24 to 48 hours, the reaction is referred to as delayed-type hypersensitivity.

In humans, exposure to a sensitizing antigen takes place upon contact with the microorganism responsible for the disease (e.g. tuberculin from Mycobacterium tuberculosis, typhoidin from Salmonella typhi and abortin from Brucella abortus), and sensitization occurs as a result of a chronic infection. In animals, sensitization can be achieved by inoculation of an antigen emulsified in water, saline or an adjuvant.

In both humans and animals, hypersensitivity is tested in vivo by the injection of the antigen dissolved in a physiologically tolerable diluent such as saline solution into the skin (either intradermally or subcutaneously). DCH is usually a more sensitive diagnostic assay than the determination or measurement of the amount of antibody produced to an antigen. For example, only minute amounts of protein (a few hundred nanograms) are necessary for DCH sensitization of a mouse, while a much larger dose is needed to induce antibody production.

Since the polypeptides of the present invention stimulate the proliferation of T cells following immunization (sensitization) with a polypeptide of the invention, a skin reaction test using one or more of the present synthetic polypeptides as a challenge antigen is employed.

Polypeptides of the invention will elicit an erythematous area and an induration of at least about 10 millimeters in diameter about the injection site, Unimmunized animals will demonstrate no DCH reaction upon intradermal injection of a polypeptide.

Production of Anti-idiotype Antibodies

Whole antibodies, or their fragments, raised against polypeptides of the present invention are of use to develop anti-idiotypic antibodies (anti-ids). These anti-ids may be monoclonal or polyclonal in nature and will specifically react with the immunizing anti-peptide antibodies. Further, the anti-ids bear the "internal image" of the nominal antigen (i.e. the polypeptides antigenic determinants) and will, when used as the immunogen, further induce an immunity to the nominal antigen. This immunity will be both humoral and cell-mediated in nature, and will effectively react with HIV antigenic determinants and result in HIV neutralization, as measured in vitro.

Monoclonal anti-ids are produced and characterized according to strategies previously reported (34, 35, 36) Balb/c mice are immunized i.p. with 50 ug of anti-peptide antibody conjugated to a carrier protein such as keyhole limpet hemocyanin (KLH), dissolved in monophosphoryl lipid A-trehalose dimycolate (MLA-TDM) and boosted on a biweekly basis with a similar does in TDM. Three days after after the third injection, spleen cells are fused with P3X63.Ag8.653 myeloma cells in the presence of polyethylene glycol. Selection of cells in HAT medium, cloning, isotype analysis and antibody purification have been described above and in the published literature (14,26).

For the detection of anti-idiotypes, microplates previously coated with purified goat anti-murine Ig are incubated with 100 ul of hybridoma supernatants for 2 hr. Excess idiotypic-negative normal mouse serum is then added for 1 hr to block excess anti-Ig. After washes with PBS-Tween 20, 100 ul of the immunogen coupled to alkaline phosphatase is added to each well for 1 hr. Following washing, wells are incubated with substrate containing p-nitrophenyl phosphate and absorbance is measured at 405 nm on an ELISA plate reader.

Anti-idiotypic antibodies directed at or near the combining site of the idiotypic-positive MABs will be identified using a competition assay: Microwells are coated with purified idiotype at 4 ug/ml, washed and then counter-coated with 1% BSA. Ten nanograms of radioiodine labeled anti-idiotype is added to the plates. Unlabeled antigen, representing the polypeptides of this invention, are preincubated with the plates for 30 minutes before the addition of labeled anti-idiotype.

Inasmuch as the anti-ids bear the internal image of the nominal antigen (i.e. the polypeptides of this invention), they may be used as immunogens to generate anti-anti-idiotypic antibodies (anti-anti-ids). Anti-anti-ids will be immunoreactive with the polypeptides of this invention and react with HIV antigenic determinants. Thus, anti-ids are effective vaccines with which to generate anti-HIV immunity and protection.

In mice, anti-anti-ids are produced by immunizing animals i.p. with 50 ug doses of anti-id-KLH conjugates in MLA-TDM. At biweekly intervals the same immunogen is administered in TDM. Sera are collected after the third boost and tested for anti-anti-id activity by means of an ELISA using microwells coated with anti-id, polypeptides of this invention or HIV antigens. Sera are also titrated for HIV neutralization using the HIV transmission assay described below.

Analysis of Sera for Activity Which Specifically Neutralizes HIV Infectivity Antipeptide anti-sera and anti-anti-id antibodies are shown to inhibit the in-vitro replication of HIV using a viral transmission assay (19). Serial dilutions of immune and pre-immune sera are mixed with $10^3$ tissue culture infectious doses/ml of HIV and incubated for 1 hr. at 4 degrees C. One ml of the mixture is then used to infect $10^7$ permissive cells in the presence of 2 ug/ml Polybrene. Permissive cells may be one of the following continuous T cells lines: Molt-3, CEM, Ti7.4 or HUT-78 (37). After a one hour incubation, the cells are washed and set up in culture. Virus spread is monitored at 10 and 20 days by measuring culture supernatant levels of reverse transcrystase and released viral antigens.

Hybridoma formation

Suitable monoclonal antibodies, typically whole antibodies, may also be prepared using hybridoma technology previously described ((27). Briefly, to form the hybridoma from which the monoclonal antibody is produced, a myeloma or other self-perpetuating cell line is fused with lymphocytes obtained from the spleen of a mammal hyperimmunized with a polypeptide of this invention.

It is preferred that the myeloma cell line be from the same species as the lymphocytes. Typically, a mouse of the strain BALB/c is the preferred mammal. Suitable mouse myelomas for use in the present invention include hypoxanthine-aminopterin-thymidine-sensitive (HAT) cell lines P3X63-Ag8.653 (ATCC CRL 580), and Sp2/0-Ag14 (ATCC CRL 1581).

Splenocytes are typically fused with myeloma cells using a polyethylene glycol such as PEG 1500 or PEG 6000. Fused hybrids are selected by their sensitivity to HAT. Hybridomas producing the antibody molecules of this invention are identified using the enzyme linked immunosorbent assay (ELISA) described in the Materials and Methods section hereinafter.

Inocula

Inocula are typically prepared from the dried solid polypeptide-conjugate or polypeptide polymer by suspending the polymer in a physiologically tolerable (acceptable) diluent such as water, saline or phosphated-buffered saline.

Inocula may also include an adjuvant. Adjuvants such as complete Freund's adjuvant (CFA), incomplete Freund's adjuvant (IFA) and alum are materials well known in the art, and are available commercially from several sources.

EXAMPLES

Monoclonal antibody production. HIV was purified from the supernatant of a producer cell line as described previously (13). Virions were disrupted in detergent-/high salt (0.5% Triton X-100/0.6M KCl) under sonication and then ether-extracted in order to remove detergent. Female Balb/c mice were primed with 100 ug of viral protein emulsified in complete Freund's adjuvant and boosted at monthly intervals with 50 ug protein in incomplete adjuvant. Three days following the fourth boost, the spleens were obtained for cell fusion. The fusion protocol, utilizing Sp2/0-Ag14 myeloma cells in the presence of 50% polyethylene glycol, was as described previously (14).

Immunologic assays. Western blotting (WB) was performed essentially as described before (13), using antigen strips provided by DuPont, Biotechnology Systems Division, Wilmington, Del. Briefly, Western blot strips were incubated for 18 hours at room temperature with MAbs at 10 ug/ml. Strips were washed in PBS-T (50 mM sodium phosphate, pH 7.2/150 mM sodium chloride/0.05% Tween-20) and then allowed to react with biotin-labeled goat antibody to murine IgG (Jackson Labs; West Grone, Pa.) for 1 hour at 37 degrees C. After washing, streptavidin-peroxidase conjugate (Jackson Labs) was applied for ½ hour at 37 degrees C. Washed strips were developed in a solution containing PBS/0.01% 4-chloro-1-naphtol/0.03% hydrogen peroxide.

Solid-phase synthetic peptides were examined for their immunoreactivity using enzyme immunoassay (EIA). Polyethylene pins, with peptides on their surface (see below), were counter-coated in EIA buffer (PBS/1% ovalbumin/1% bovine serum albumin/0.1% Tween-20) for 18 hours at 4 degrees C. After washing with PBS-T (4×10 min), the pins were incubated in microplates containing MAb or control antibody, each at 10 ug/ml, for 18 hours at 4° C. After washing as above, incubation was allowed to proceed for 1 hour in enzyme-conjugated antiglobulin (anti-murine IgG: peroxidase; Jackson Labs). The washed pins were next immersed into wells containing ABTS substrate solution (azino-bis-3-ethylbenzthiazoline-6-sulfonic acid, 0.5 mg/ml in pH 4.0 citrate buffer/0.03% hydrogen peroxide). Reactions were stopped after 30 minutes by removing the pins and absorbance measurements were taken at 450 nm using a microplate reader.

Competitive inhibition experiments were performed with soluble, synthetic peptides dissolved in PBS-T. Solid-phase target antigen represented 96-well microplates which were coated with HIV (5 ug/ml) for 18 hours at 4 degrees C. For competition analysis, various concentrations of synthetic peptides were allowed to react within HIV-coated microwells in the presence of biotin-labeled MAbs for 90 minutes at 37 degrees C. Biotin derivitization was performed using N-hydroxysuccinimide-d-biotin (Calbiochem, La Jolla, Calif.) (15). The concentration of biotin-MAb chosen corresponded to approximately 40% of maximal binding activity. After aspiration of the probe:inhibitor mixture, the wells were washed five times with PBS-T and streptavidin-peroxidase (Jackson Labs) was added for a further 30 minutes. Thereafter, washed wells received ABTS substrate solution and absorbance was monitored as above. Specific inhibition was calculated according to the formula:

$$\% \text{ specific inhibition} = 100 \times (A \max - Ax) / (A \max - A \min)$$

where, A max=maximal absorbance in the presence of buffer; A min=minimal (background) absorbance in the presence of specific inhibitor (10 ug/ml of homologous, unlabeled MAb); Ax=absorbance in the presence of the test peptide.

Epitope scanning. The strategy employed consisted of the construction of sequential, overlapping hexapeptides which completely spanned the entire HIV p17 amino acid sequence (16). Since the anti-p17 MAbs under study strongly reacted with the prototype HTLV-IIIB strain of HIV, its published sequences were used to construct peptide homologs (17). Peptides were synthesized in situ on plastic pins which conform in configuration to a standard 96-well microplate, using reagents and a kit (Epitope Mapping Kit) provided by Cambridge Research Biochemicals, Inc., Valley Stream, N.Y. After step-wise, solid-phase syntheses, the peptides were de-protected (20%) piperidine in dimethyl formamide), washed and air-dried. Included in the experiment was the use of concurrently-synthesized peptide controls with known reactivity versus available antisera. These peptides represented the sequences Pro Leu Ala Gln and Gly Leu Ala Gln. One of these peptides (Pro Leu Ala Gln) is known to react with antibody to sperm whale myoglobin, while the other is non-reactive but similar in structure. These EIA-testable peptides were included in each assay run.

Soluble, synthetic peptides. Peptides were synthesized following the strategy of Merrifield (18) at Peninsula Laboratories, Inc., Belmont, Calif. The acid-labile, tert-butyloxycarbonyl group was used for temporary amino-terminal protection. Peptides were cleaved from the resin using HF/anisole (9:1) containing 2% ethanedithiol and purified by gel filtration (Sephadex G-25 in 0.1M acetic acid) followed by reversed-phase high performance liquid chromatography. The sequence of each peptide was confirmed using amino acid analysis.

HIV infectivity assay. Serial dilutions of various MAbs or control antibodies were mixed with $10^3$ TCID$_{50}$ doses (19) of infectious HIV and incubated for 1 hour at 4 degrees C. One ml of the mixture was utilized to infect $1 \times 10^6$ permissive HUT-102 cells in the presence of polybrene (2 ug/ml in RPMI-1640). After a one hour incubation at 37 degrees C. the cells were washed and placed in culture in complete medium containing RPMI-1640/10% fetal bovine serum/antibiotics. Virus spread was monitored at 10 days by measuring reverse transcriptase (20).

For some experiments, peripheral blood mononuclear cells, pre-stimulated with phytohemagglutinin (PHA) were employed as the permissive cell substrate, as previously described (21). In brief, washed lymphocytes at $1 \times 10^6$ cells/ml were incubated for 3 days in the presence of 1 ug/ml PHA-P (Defco, Detroit, Mich.). Thereafter, the washed cells were resuspended in infectivity media [complete medium containing 10% interleukin-2 (Cellular Products, Inc.), and 2 ug/ml Polybrene]. The lymphocyte cultures containing activated T-cells were then employed for viral transmission experiments.

Results

Spleen cells from an animal immunized with HIV lysate were subjected to cell fusion and the resultant crude hybridoma cultures were screened for antibody activity using solid-phase EIA and WB. Cultures of interest were cloned, re-assayed and subcloned. Three cloned lines were studied in more detail; two hybridomas secreted anti-p17 antibodies (clones 32/5.8/42 and 32/1.24.89) and one produced antibody reactive with p24 (clone 32/5.17.76), each of the IgG class of immunoglobulin. On WB examination (FIG. 1), the p17 MAbs bound to polyprotein precursor in addition to mature viral core protein. No cross-reactivity was observed with HTLV-I infected T-cells.

Figure 2:
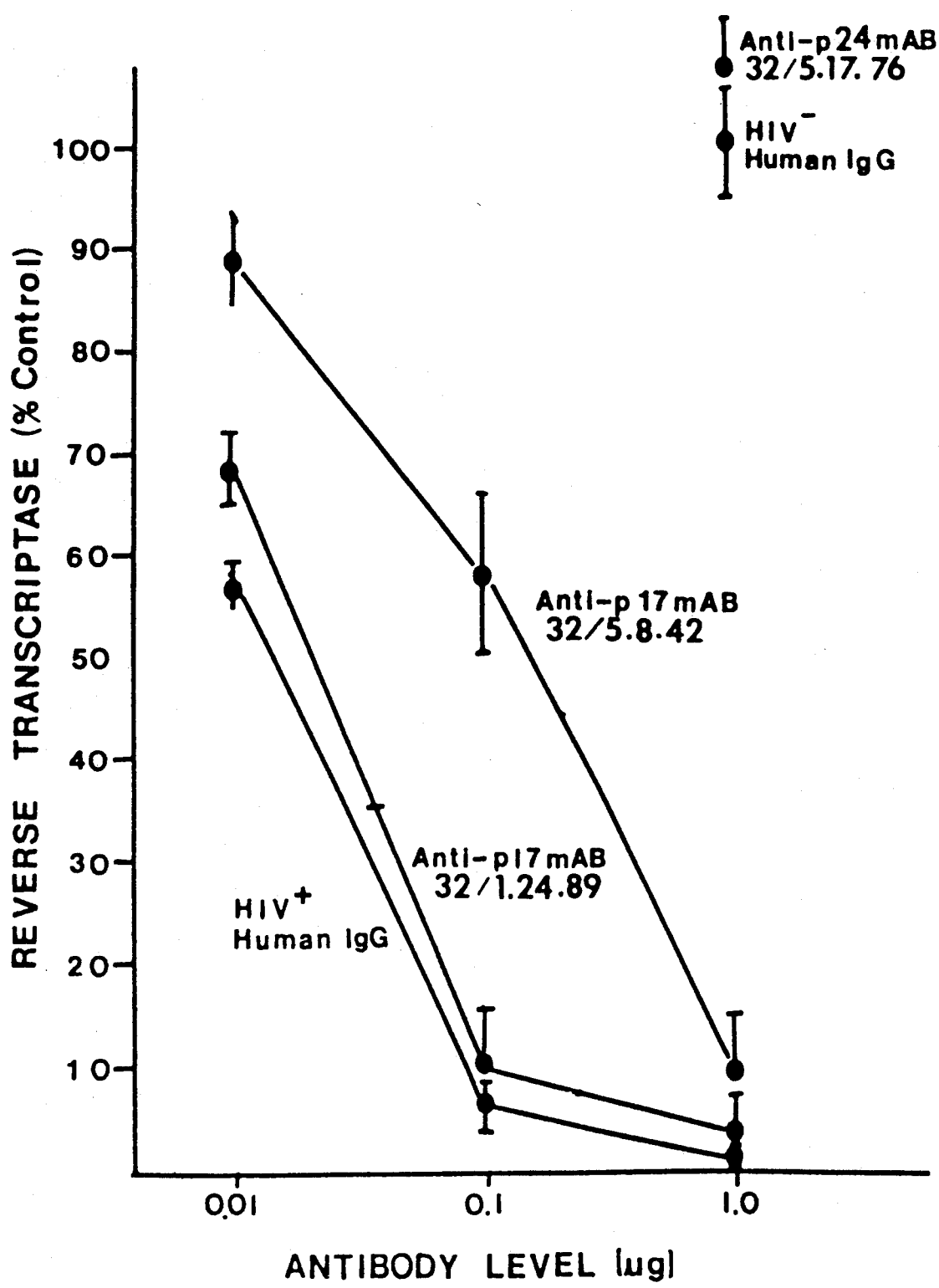
Figure 3:
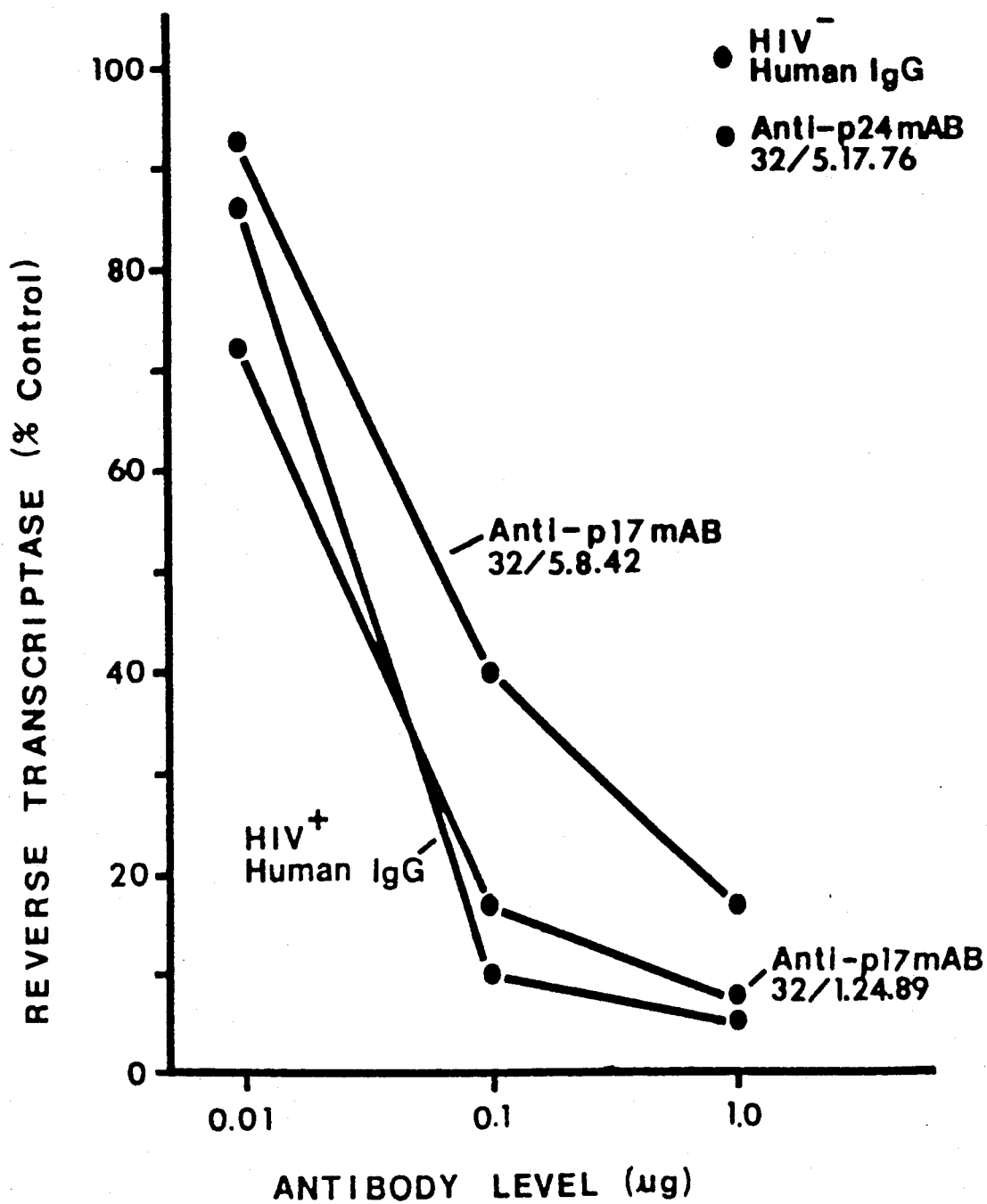

In order to study the biological activity of the MAbs, HIV infectivity assays were performed. Assays were performed using cell-free virus which was allowed to propagate in HUT-102 permissive cells. In addition to the anti-core MAbs, the neutralizing capacity of IgG purified from seropositive (HIV+ IgG) and seronegative (HIV−IgG) donors was evaluated. As shown in FIG. 2, MAb 32/5.17.76 (anti-p24) and HIV-IgG failed to perturb the infectivity of cell-free virus. In contrast, submicrogram concentrations of HIV+ IgG and MAb 32/1.24.89 were potent inhibitors of viral replication. The other anti-p17 antibody (MAb 32/5.8/42) also demonstrated a significant level of viral inhibition, although at higher input levels of immunoglobulin. Indistinguishable results were obtained when PHA-stimulated peripheral blood lymphocytes were employed as the permissive cell (FIG. 3), indicating that antibody-mediated viral inhibition was a cell substrate-independent event.

To determine if the two MAb reagents against p17 were identifying the same antigenic site on the core protein, antibody competition assays were run. As seen in FIG. 4, the reactivity of biotin-conjugated MAb 32/1.24.89 versus solid-phase HIV was undisturbed in the presence of 1000-fold excess levels of anti-p24 MAb. In contrast, complete binding inhibition was observed with homologous, unlabeled antibody 32/1.24.89. Of interest, anti-p17 MAb 32/5.8.42 also produced a significant inhibition (approximately 80%), indicating that these antibodies reacted with sterically-related epitopes of the p17 molecule. Reciprocal inhibition experiments (FIG. 4, bottom) yielded similar data.

Figure 5:
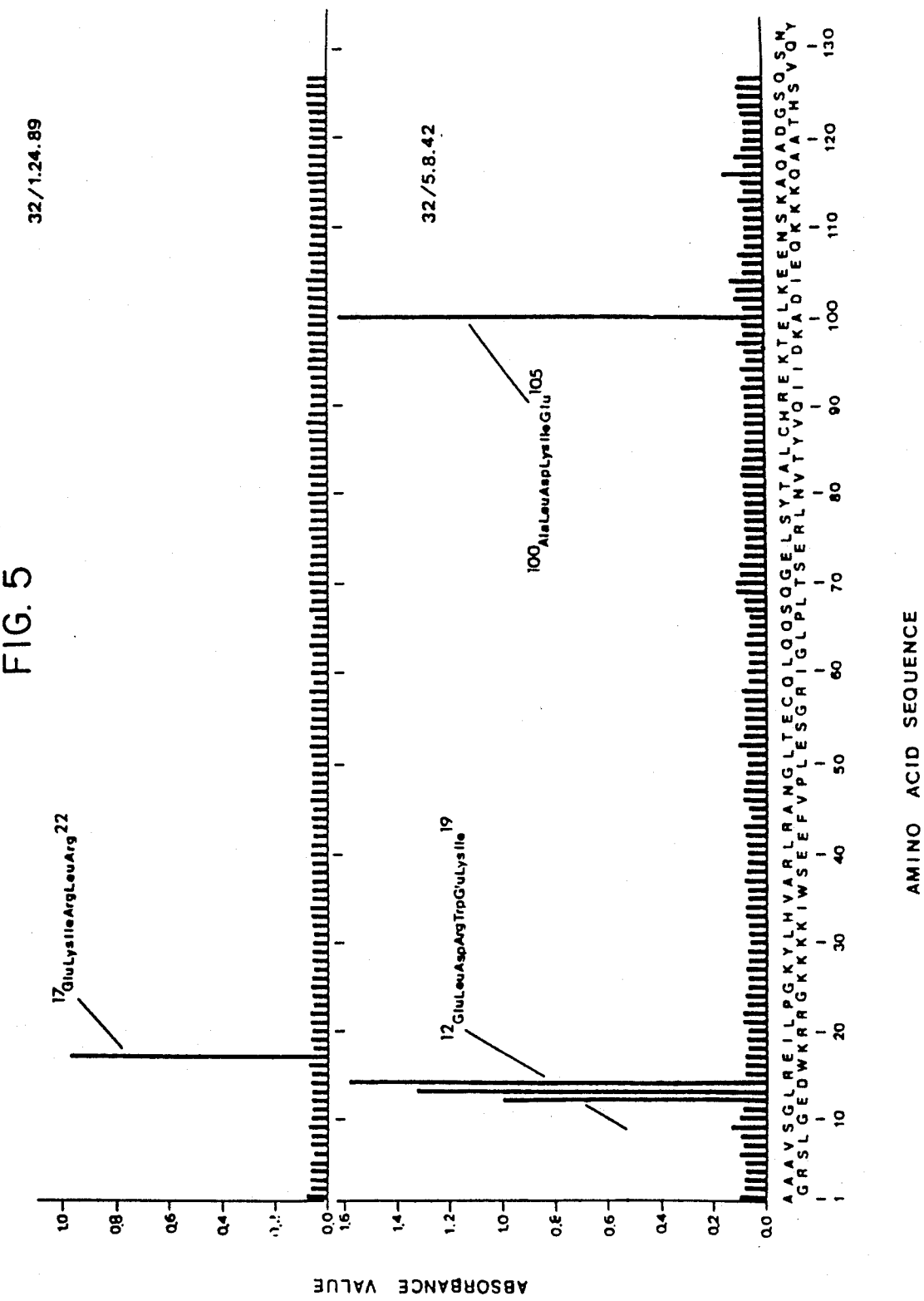

To precisely define the p17 epitopes of interest, epitope scanning was performed using a series of overlapping, hexapeptides which completely spanned the HIV p17 gene product. The solid-phase peptides were individually screened for their reactivity against each p17 MAb using EIA (FIG. 5). Results clearly indicated that MAb 32/5.8.42 strongly bound to 3 adjacent peptides occupying the amino-terminal region of p17 and to a single hexapeptide much further downstream. Antibody 32/1.24.89 produced a distinct pattern of binding (FIG. 5); that MAb strongly bound to a single peptide which partially overlapped the antigenic region recognized by MAb 32/5.8.42. No downstream binding was observed with MAb 32/1.24.89.

Figure 6:
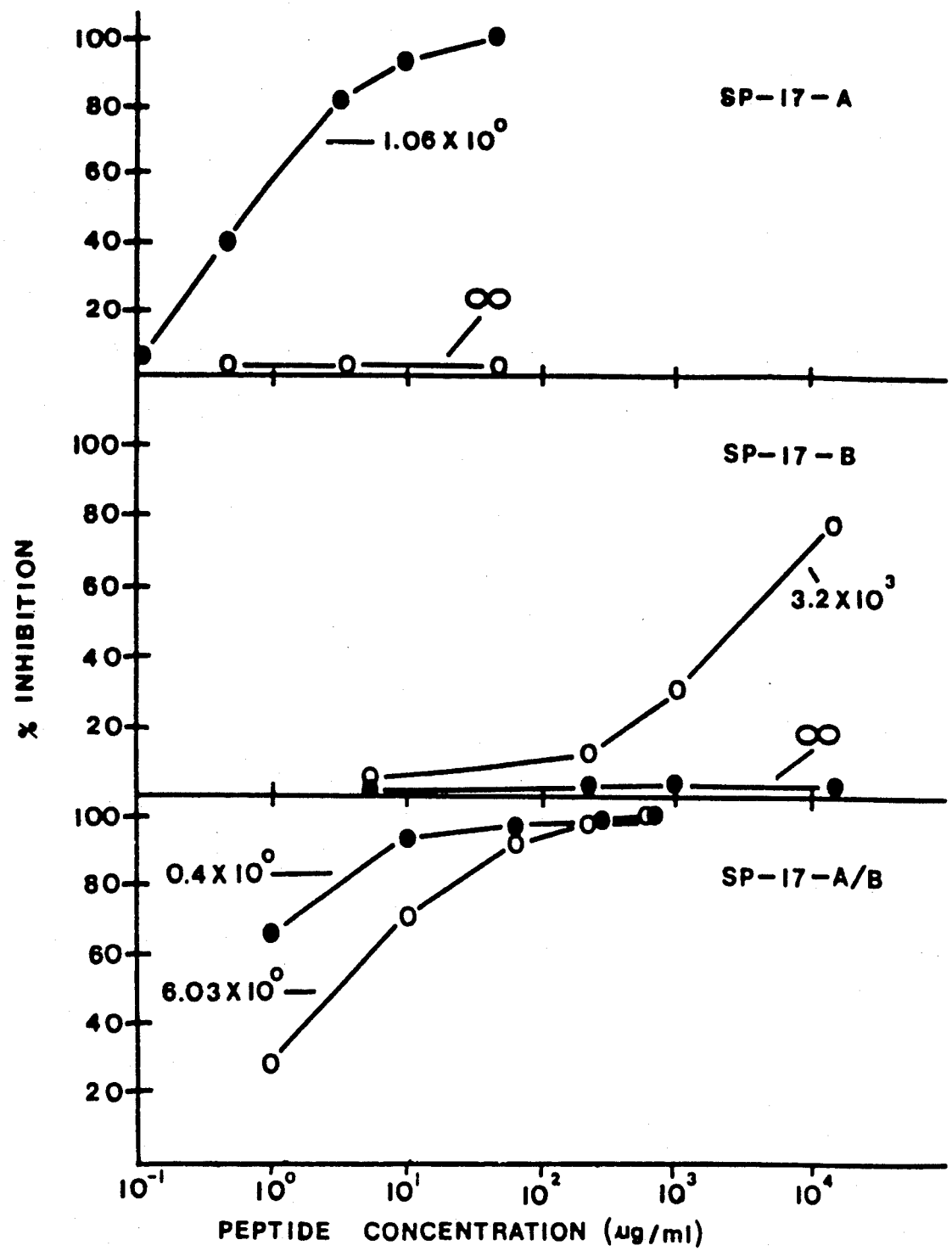

To confirm the data obtained from epitope scanning experiments, soluble peptides were synthesized which corresponded to the amino-terminal, MAb 32/5.8.42-binding site (epitope "A"; residues 12-19); the MAb 32/1.24.89-binding site (epitope "B"; residues 17-22); and to a region containing both binding sites (epitope "A/B"; residues 12-22): these synthetic peptides were termed SP-17-A, SP-17-B and SP-17-A/B, respectively. At the experimental level, each soluble peptide was allowed to compete with solid-phase HIV for the binding of both MAbs. As shown in FIG. 6, SP-17-A effectively inhibited the binding activity of MAb 32/5.8.42, exhibiting an $ID_{50}$ dose of approximately 1 ug/ml. This peptide was immunologically specific, inasmuch as no effect was noted on the reactivity of MAb 32/1.24.89. SP-17-B, corresponding to the binding site of MAb 32/1.24.89, was capable of inhibiting homologous antibody but only at very high concentrations ($ID_{50}$ of approximately $3.2 \times 10^3$ ug/ml), indicating a low affinity interaction. However, the inhibition was immunologically specific. Further studies was a synthetic peptide which contained both MAb binding sites. This peptide, SP-17-A/B was a strong inhibitor of each anti-p17 antibody (FIG. 6). The $ID_{50}$ dose versus MAb 32/5.8.42 was similar to that observed with SP-17-A (0.4 versus 1.06 ug/ml). In distinction, SP-7-A/B was almost 500 times more effective than SP-17-B with respect to its capacity to compete MAb 32/1.24.89 ($ID_{50}$ dose 6.03 ug/ml versus $3.2 \times 10^3$ ug/ml). Of the three synthetic peptides studied, none demonstrated any detechable inhibition of an irrelevant MAb (anti-HIV p24, clone 32/5.17.76), at dose ranges of up to $10^3$ ug/ml.

LITERATURE CITED

1. Ho et al, J. Virol. 61:2024 (1987).
2. Prince et al, J. Infect. Dis. 156:268 (1987).
3. Wendler et al, AIDS Res. Human Retroviruses 3:157 (1987).
4. Matsushita et al, J. Virol. 62:2107 (1988).
5. Lasky et al, Science 233:209 (1986).
6. Krohn et al Proc. Natl. Acad. Sci. U.S.A. 84:4994 (1987).
7. Palker et al, Proc. Natl. Acad. Sci. U.S.A. 85:1932 (1988).
8. Ho et al, Science 239:1021 (1988).
9. Chanh et al, Proc. Natl. Acad. Sci. U.S.A. 84:3891 (1987).
10. Veronese et al, J. Virol. 62:795 (1988).
11. Sarin et al, Science 232:1135 (1986).
12. Naylor et al, Proc. Natl. Acad. Sci. U.S.A. 84:2951 (1987).
13. Papsidero et al, Hybridoma 7:117 (1988).
14. Papsidero et al, Cancer Res. 43:1741 (1983).
15. Guesdon et al, J. Histochem. Cytochem. 27:1131 (1979).
16. Geysen et al, J. Immunol. Methods 102:259 (1987).
17. Ratner et al, Nature 313:277 (1985).
18. Merrifield, J. Am. Chem. Soc. 85:2149 (1983).
19. Walker et al, Science 234:1563 (1986).
20. Eho et al, Virol. 112:355 (1981).
21. Folks et al, J. Immunol. 136:4049 (1986).
22. Ritter et al, Immunol. Letters 16:97 (1987).
23. Alizon et al, Cell 46:63 (1986).
24. Sanchez-Pescador et al, Science 227:484 (1985).
25. Wain-Hobson et al, Cell 40:9 (1985).
26. Papsidero et al, Hybridoma 2:139 (1983).
28. Sarin et al, Science 232:1135 (186).
29. Koprowski, Cancer Res. 45, 4869s (1985).
30. Houghten et al., Int. J. Pept. Prot. Res 16:311 (1980).
31. Ellman, Arch. Biochem. Biophys. 82:70 (1959).]
32. Liu et al., Biochem., 80:690 (1979).
33. Klipstein et al., J. Infect. Dis 147:318 (1983).
34. Reilly et al., Hybridoma 6:461 (1987).
35. McNamara-Ward, J. Immunology 139:2775 (1987).
36. Nelson et al., J. Immunology 139:2110 (1987)).
37. Gallo, R. C. et. al., U.S. Pat. No. 4,652,599 issued Mar. 24, 1987.

What is claimed is:

1. A protein that consists of at least one polypeptide selected from the group consisting of Glu-Leu-Asp-Arg-Trp-Glu-Lys-Ile, defined in the sequence listing as SEQ ID NO:1, Glu-Leu-Asp-Arg-Trp-Glu, defined in the sequence listing as SEQ ID NO:2, Leu-Asp-Arg-Trp-Glu-Lys, defined in the sequence listing as SEQ ID NO:3, Asp-Arg-Trp-Glu-Lys-Ile, defined in the sequence listing as SEQ ID NO:4, Glu-Lys-Ile-Arg-Leu-Arg, defined in the sequence listing as SEQ ID NO:5, and Glu-Leu-Asp-Arg-Trp-Glu-Lys-Ile-Arg-Leu-Arg, defined in the sequence listing as SEQ ID NO:6, provided that said protein is not one found in a naturally occurring human immunodeficiency virus or other animal virus.

2. A protein that consists of at least one polypeptide selected from the group consisting of Glu-Leu-Asp-Arg-Trp-Glu-Lys-Ile, defined in the sequence listing as SEQ ID NO:1, Glu-Leu-Asp-Arg-Trp-Glu, defined in the sequence listing as SEQ ID NO:2, Leu-Asp-Arg-Trp-Glu-Lys, defined in the sequence listing as SEQ ID NO:3, Asp-Arg-Trp-Glu-Lys-Ile, defined in the sequence listing as SEQ ID NO:4, Glu-Lys-Ile-Arg-Leu-Arg, defined in the sequence listing as SEQ ID NO:5, and Glu-Leu-Asp-Arg-Trp-Glu-Lys-Ile-Arg-Leu-Arg, defined in the sequence listing as SEQ ID NO:6, as an immunogen in order to produce either antibodies with reactivity against a portion of human immunodeficiency virus (HIV) or cells capable of producing said antibodies provided said protein is not part of naturally occurring HIV or other animal virus.

3. An immunization inoculum consisting essentially of a protein of claim 1.

4. A substantially pure preparation of a protein of claim 1.

5. A protein of claim 1, the selected polypeptide being one with the amino acid sequence defined in the Sequence Listing by SEQ ID NO:5.

6. A protein of claim 1, the selected polypeptide being one with the amino acid sequence defined in the Sequence Listing by SEQ ID NO:1.

7. A protein of claim 5 further provided that, in said protein, a polypeptide linked by a peptide bond to either end of said selected polypeptide does not have the same amino acid sequence as a polypeptide that, in naturally occurring human immunodeficiency virus p17 protein, is linked to an end of a polypeptide with the amino sequence defined in the Sequence listing by SEQ ID NO:5.

8. A protein of claim 6 further provided that, in said protein, a polypeptide linked by a peptide bond to either end of said selected polypeptide does not have the same amino acid sequence as a polypeptide that, in naturally occurring human immunodeficiency virus p17 protein, is linked to an end of a polypeptide with the amino sequence defined in the Sequence listing by SEQ ID NO:1.

9. A protein of claim 1, said selected polypeptide being one with the amino acid sequence defined in the Sequence Listing by SEQ ID NO:2 provided that, in said protein, a polypeptide linked by a peptide bond to either end of said selected polypeptide does not have the same amino acid sequence as a polypeptide that, in naturally occurring human immunodeficiency virus p17 protein, is linked to an end of a polypeptide with the amino sequence defined in the Sequence listing by SEQ ID NO:2.

10. A protein of claim 1, said selected polypeptide being one with the amino acid sequence defined in the Sequence Listing by SEQ ID NO:3 provided provided that, in said protein, a polypeptide linked by a peptide bond to either end of said selected polypeptide does not have the same amino acid sequence as a polypeptide that, in naturally occurring human immunodeficiency virus p17 protein, is linked to an end of a polypeptide with the amino sequence defined in the Sequence listing by SEQ ID NO:3.

11. A protein of claim 1, said selected polypeptide being one with the amino acid sequence defined in the Sequence Listing by SEQ ID NO:4 provided that, in said protein, a polypeptide linked by a peptide bond to either end of said selected polypeptide does not have the same amino acid sequence as a polypeptide that, in naturally occurring human immunodeficiency virus p17 protein, is linked to an end of a polypeptide with the amino sequence defined in the Sequence listing by SEQ ID NO:4.

12. A protein of claim 1, said selected polypeptide being one with the amino acid sequence defined in the Sequence Listing by SEQ ID NO:6 provided that, in said protein, a polypeptide linked by a peptide bond to either end of said selected polypeptide does not have the same amino acid sequence as a polypeptide that, in naturally occurring human immunodeficiency virus p17 protein, is linked to an end of a polypeptide with the amino sequence defined in the Sequence listing by SEQ ID NO:6.

13. A process of inducing an immune system response which comprises the step of administering to a nonhuman mammal a protein that consist of at least one polypeptide selected from the group consisting of those with amino acid sequences defined in the Sequence Listing by SEQ ID NO:1, SEQ ID NO:2, SEQ ID NO:3, SEQ ID NO:4, SEQ ID NO:5, and SEQ ID NO:6, respectively, provided that said protein is not one found in a naturally occurring human immunodeficiency virus or other animal virus.

14. A process of claim 13, the selected polypeptide being one with the amino acid sequence defined in the Sequence Listing by SEQ ID NO:5.

15. A process of claim 13, the selected polypeptide being one with the amino acid sequence defined in the Sequence Listing by SEQ ID NO:1.

16. A process of claim 13 further provided that, in said protein, a polypeptide linked by a peptide bond to either end of said selected polypeptide does not have the same amino acid sequence as a polypeptide that, in naturally occurring human immunodeficiency virus p17 protein, is linked to an end of a polypeptide with the amino sequence defined in the Sequence listing by SEQ ID NO:5.

17. A process of claim 15 further provided that, in said protein, a polypeptide linked by a peptide bond to either end of said selected polypeptide does not have the same amino acid sequence as a polypeptide that, in naturally occurring human immunodeficiency virus p17 protein, is linked to an end of a polypeptide with the amino sequence defined in the Sequence listing by SEQ ID NO:1.

18. A process of claim 13, said selected polypeptide being one with the amino acid sequence defined in the Sequence Listing by SEQ ID NO:2 provided that, in said protein, a polypeptide linked by a peptide bond to either end of said selected polypeptide does not have the same amino acid sequence as a polypeptide that, in naturally occurring human immunodeficiency virus p17 protein, is linked to an end of a polypeptide with the amino sequence defined in the Sequence listing by SEQ ID NO:2.

19. A process of claim 13, said selected polypeptide being one with the amino acid sequence defined in the Sequence Listing by SEQ ID NO:3 provided that, in said protein, a polypeptide linked by a peptide bond to either end of said selected polypeptide does not have the same amino acid sequence as a polypeptide that, in naturally occurring human immunodeficiency virus p17 protein, is linked to an end of a polypeptide with the amino sequence defined in the Sequence listing by SEQ ID NO:3.

20. A process of claim 13, said selected polypeptide being one with the amino acid sequence defined in the Sequence Listing by SEQ ID NO:4 provided that, in said protein, a polypeptide linked by a peptide bond to either end of said selected polypeptide does not have the same amino acid sequence as a polypeptide that, in naturally occurring human immunodeficiency virus p17 protein, is linked to an end of a polypeptide with the amino sequence defined in the Sequence listing by SEQ ID NO:4.

21. A process of claim 13, said selected polypeptide being one with the amino acid sequence defined in the Sequence Listing by SEQ ID NO:6 provided that, in said protein, a polypeptide linked by a peptide bond to either end of said selected polypeptide does not have the same amino acid sequence as a polypeptide that, in naturally occurring human immunodeficiency virus p17 protein, is linked to an end of a polypeptide with the amino sequence defined in the Sequence listing by SEQ ID NO:6.

22. A process of claim 13 which further comprises the step of producing from the nonhuman mammal, either or both of the following: (1) antibodies that react with said selected polypeptide or (2) cells capable of producing antibodies that react with said polypeptide.

23. A process of claim 22, the selected polypeptide being one with the amino sequence defined in the Sequence Listing by SEQ ID NO:5.

24. A process of claim 22, the selected polypeptide being one with the amino acid sequence defined in the Sequence Listing by SEQ ID NO:1.

25. A process of claim 23 further provided that, in said protein, a polypeptide linked by a peptide bond to either end of said selected polypeptide does not have the same amino acid sequence as a polypeptide that, in naturally occurring human immunodeficiency virus p17 protein, is linked to an end of a polypeptide with the amino sequence defined in the Sequence listing by SEQ ID NO:5.

26. A process of claim 24 further provided that, in said protein, a polypeptide linked by a peptide bond to either end of said selected polypeptide does not have the same amino acid sequence as a polypeptide that, in naturally occurring human immunodeficiency virus p17 protein, is linked to an end of a polypeptide with the amino sequence defined in the Sequence listing by SEQ ID NO:1.

27. A process of claim 22, said selected polypeptide being one with the amino acid sequence defined in the Sequence Listing by SEQ ID NO:2 provided that, in said protein, a polypeptide linked by a peptide bond to either end of said selected polypeptide does not have the same amino acid sequence as a polypeptide that, in naturally occurring human immunodeficiency virus p17 protein, is linked to an end of a polypeptide with the amino sequence defined in the Sequence listing by SEQ ID NO:2.

28. A process of claim 22, said selected polypeptide being one with the amino acid sequence defined in the Sequence Listing by SEQ ID NO:3 provided that, in said protein, a polypeptide linked by a peptide bond to either end of said selected polypeptide does not have the same amino acid sequence as a polypeptide that, in naturally occurring human immunodeficiency virus p17 protein, is linked to an end of a polypeptide with the amino sequence defined in the Sequence listing by SEQ ID NO:3.

29. A process of claim 22, said selected polypeptide being one with the amino acid sequence defined in the Sequence Listing by SEQ ID NO:4 provided that, in said protein, a polypeptide linked by a peptide bond to either end of said selected polypeptide does not have the same amino acid sequence as a polypeptide that, in naturally occurring human immunodeficiency virus p17 protein, is linked to an end of a polypeptide with the amino sequence defined in the Sequence listing by SEQ ID NO:4.

30. A process of claim 22, said selected polypeptide being one with the amino acid sequence defined in the Sequence Listing by SEQ ID NO:6 provided that, in said protein, a polypeptide linked by a peptide bond to either end of said selected polypeptide does not have the same amino acid sequence as a polypeptide that, in naturally occurring human immunodeficiency virus p17 protein, is linked to an end of a polypeptide with the amino sequence defined in the Sequence listing by SEQ ID NO:6.

31. The process of claim 13 in which the protein is administered to a nonhuman mammal and, subsequent to the time the protein is administered, the antibodies of said nonhuman mammal subjected to an immunological assay which will reveal the presence of antibodies against the polypeptide selected from the group consisting of those with amino acids defined in the Sequence Listing by SEQ ID NO:1, SEQ ID NO:2, SEQ ID NO:3, SEQ ID NO:4, SEQ ID NO:5 and SEQ ID NO:6.

32. The process of claim 31, the selected polypeptide being one with the amino acid sequence defined in the Sequence Listing by SEQ ID NO:5.

33. A process of claim 31, the selected polypeptide being one with the amino acid sequence defined in the Sequence Listing by SEQ ID NO:1.

34. A process of claim 32 further provided that, in said protein, a polypeptide linked by a peptide bond to either end of said selected polypeptide does not have the same amino acid sequence as a polypeptide that, in naturally occurring human immunodeficiency virus p17 protein, is linked to an end of a polypeptide with the amino sequence defined in the Sequence listing by SEQ ID NO:5.

35. A process of claim 33 further provided that, in said protein, a polypeptide linked by a peptide bond to either end of said selected polypeptide does not have the same amino acid sequence as a polypeptide that, in naturally occurring human immunodeficiency virus p17 protein, is linked to an end of a polypeptide with the amino sequence defined in the Sequence listing by SEQ ID NO:1.

36. A process of claim 31, said selected polypeptide being one with the amino acid sequence defined in the Sequence Listing by SEQ ID NO:2 provided that, in said protein, a polypeptide linked by a peptide bond to either end of said selected polypeptide does not have the same amino acid sequence as a polypeptide that, in naturally occurring human immunodeficiency virus p17 protein, is linked to an end of a polypeptide with the amino sequence defined in the Sequence listing by SEQ ID NO:2.

37. A process of claim 31, said selected polypeptide being one with the amino acid sequence defined in the Sequence Listing by SEQ ID NO:3 provided that. in said protein, a polypeptide linked by a peptide bond to either end of said selected polypeptide does not have the same amino acid sequence as a polypeptide that, in naturally occurring human immunodeficiency virus p17 protein, is linked to an end of a polypeptide with the amino sequence defined in the Sequence listing by SEQ ID NO:3.

38. A process of claim 31, said selected polypeptide being one with the amino acid sequence defined in the Sequence Listing by SEQ ID NO:4 provided that, in said protein, a polypeptide linked by a peptide bond to either end of said selected polypeptide does not have the same amino acid sequence as a polypeptide that, in naturally occurring human immunodeficiency virus p17 protein, is linked to an end of a polypeptide with the amino sequence defined in the Sequence listing by SEQ ID NO:4.

39. A process of claim 31, said selected polypeptide being one with the amino acid sequence defined in the Sequence Listing by SEQ ID NO:6 provided that, in said protein, a polypeptide linked by a peptide bond to either end of said selected polypeptide does not have the same amino acid sequence as a polypeptide that, in naturally occurring human immunodeficiency virus p17 protein, is linked to an end of a polypeptide with the amino sequence defined in the Sequence listing by SEQ ID NO:6.

40. A substantially pure preparation of a protein of claim 5.

41. A substantially pure preparation of a protein of claim 6.

42. A substantially pure preparation of a protein of claim 7.

43. A substantially pure preparation of a protein of claim 8.

44. A substantially pure preparation of a protein of claim 9.

45. A substantially pure preparation of a protein of claim 10.

46. A substantially pure preparation of a protein of claim 11.

47. A substantially pure preparation of a protein of claim 12.

48. A protein of claim 1 provided further that, in said protein, a polypeptide linked by a peptide bond to either end of a polypeptide selected from the group does not have the same amino acid sequence as a polypeptide that, in naturally occurring human immunodeficiency virus p17 protein, is linked to an end of the polypeptide selected from the group.

49. A protein of claim 13 provided further that, in said protein, a polypeptide linked by a peptide bond to either end of a polypeptide selected from the group does not have the same amino acid sequence as a polypeptide that, in naturally occurring human immunodeficiency virus p17 protein, is linked to an end of the polypeptide selected from the group.

50. The process of claim 49 which further comprises the step of isolating antibodies from the serum of the nonhuman mammal, either or both of the following: antibodies that react with said selected polypeptide or cells capable of producing antibodies that react with said polypeptide.

51. The process of claim 50 in which the protein is administered to a nonhuman mammal and which further comprises the step of subjecting the antibodies to an immunological assay which will reveal the presence of antibodies against the polypeptide selected.

52. A substantially pure preparation of a protein of claim 48.

* * * * *

UNITED STATES PATENT AND TRADEMARK OFFICE
CERTIFICATE OF CORRECTION

PATENT NO. : 5,185,147

DATED : February 9, 1993

INVENTOR(S) : Papsidero

It is certified that error appears in the above-identified patent and that said Letters Patent is hereby corrected as shown below:

```
Column 1, line 46 "residues" should read --resides--;
         line 49 "#88-115" should read --#81-115--.
Column 4, line 64 "crating" should read --creating--.
Column 13, line 19 "synthesis" should read --syntheses--.
Column 14, line 43 "Lie" should read --Liu--.
Column 24, line 6 delete second occurrence of "provided".
```

Signed and Sealed this

Eighth Day of March, 1994

Attest:

BRUCE LEHMAN

Attesting Officer

Commissioner of Patents and Trademarks